US008758408B2

(12) United States Patent
Chin et al.

(10) Patent No.: US 8,758,408 B2
(45) Date of Patent: Jun. 24, 2014

(54) SPINOUS PROCESS FIXATION IMPLANT

(75) Inventors: Kingsley Richard Chin, Philadelphia, PA (US); Daniel R. Baker, Seattle, CA (US); Daniel F. Justin, Logan, UT (US)

(73) Assignee: Spinefrontier Inc, Beverly, MA (US)

( * ) Notice: Subject to any disclaimer, the term of this patent is extended or adjusted under 35 U.S.C. 154(b) by 2054 days.

(21) Appl. No.: 11/609,988

(22) Filed: Dec. 13, 2006

(65) Prior Publication Data

US 2007/0179500 A1 Aug. 2, 2007

Related U.S. Application Data

(63) Continuation of application No. 11/609,418, filed on Dec. 12, 2006.

(60) Provisional application No. 60/750,520, filed on Dec. 14, 2005.

(51) Int. Cl.
*A61B 17/70* (2006.01)

(52) U.S. Cl.
USPC .......................................... 606/248; 606/249

(58) Field of Classification Search
USPC ................... 606/71, 248, 249, 282, 284, 297; 623/17.11, 17.15, 17.16, 17.12–17.14
See application file for complete search history.

(56) References Cited

U.S. PATENT DOCUMENTS

| | | | | |
|---|---|---|---|---|
| 2,781,687 A | * | 2/1957 | Knocke | 411/11 |
| 4,554,914 A | * | 11/1985 | Kapp et al. | 606/86 A |
| 5,011,484 A | * | 4/1991 | Breard | 606/249 |
| 5,180,381 A | | 1/1993 | Aust et al. | |
| 5,496,318 A | * | 3/1996 | Howland et al. | 606/249 |
| 5,645,599 A | | 7/1997 | Samani | |
| 6,214,050 B1 | * | 4/2001 | Huene | 623/17.15 |
| 6,312,431 B1 | * | 11/2001 | Asfora | 606/279 |
| 6,440,169 B1 | * | 8/2002 | Elberg et al. | 623/17.16 |
| 7,011,685 B2 | * | 3/2006 | Arnin et al. | 623/17.16 |
| 7,442,208 B2 | * | 10/2008 | Mathieu et al. | 623/17.11 |
| 2003/0040746 A1 | * | 2/2003 | Mitchell et al. | 606/61 |
| 2003/0163132 A1 | * | 8/2003 | Chin | 606/61 |
| 2003/0216736 A1 | | 11/2003 | Robinson et al. | |
| 2004/0002764 A1 | * | 1/2004 | Gainor et al. | 623/17.16 |
| 2004/0106995 A1 | * | 6/2004 | Le Couedic et al. | 623/17.11 |
| 2004/0186475 A1 | * | 9/2004 | Falahee | 606/61 |
| 2005/0060036 A1 | | 3/2005 | Schultz et al. | |
| 2005/0075634 A1 | * | 4/2005 | Zucherman et al. | 606/61 |
| 2005/0101955 A1 | * | 5/2005 | Zucherman et al. | 606/61 |
| 2005/0102028 A1 | * | 5/2005 | Arnin et al. | 623/17.13 |
| 2005/0131409 A1 | * | 6/2005 | Chervitz et al. | 606/61 |
| 2005/0203512 A1 | * | 9/2005 | Hawkins et al. | 606/61 |

(Continued)

*Primary Examiner* — Jerry Cumberledge
(74) *Attorney, Agent, or Firm* — AKC Patents LLC; Aliki K. Collins

(57) ABSTRACT

An implantable spinous process fixation device includes a k-shaped component comprising an elongated plate and top and bottom deformable plates extending at first and second angles from a first surface of the elongated plate, respectively, thereby defining first and second spaces between the elongated plate and the top and bottom deformable plates and a compression element configured to compress and move the first and second deformable plates toward the elongated plate and to change the first and the second angles, respectively. The first and second spaces are configured to receive first and second spinous processes, respectively. Compressing and moving the first and second deformable plates toward the elongated plate results in engaging the first surface of the elongated plate and first surfaces of the top and bottom deformable plates with lateral surfaces of the first and second spinous processes, respectively.

24 Claims, 31 Drawing Sheets

(56) References Cited

U.S. PATENT DOCUMENTS

| | | | |
|---|---|---|---|
| 2005/0216011 A1* | 9/2005 | Paul | 606/69 |
| 2005/0245937 A1* | 11/2005 | Winslow | 606/90 |
| 2005/0261768 A1* | 11/2005 | Trieu | 623/17.11 |
| 2005/0267579 A1* | 12/2005 | Reiley et al. | 623/17.11 |
| 2006/0015181 A1 | 1/2006 | Elberg | |
| 2006/0247640 A1 | 11/2006 | Blackwell et al. | |
| 2006/0282075 A1* | 12/2006 | Labrom et al. | 606/61 |
| 2007/0067040 A1* | 3/2007 | Ferree | 623/17.16 |
| 2007/0093823 A1* | 4/2007 | Booth et al. | 606/61 |
| 2007/0161992 A1* | 7/2007 | Kwak et al. | 606/61 |

* cited by examiner

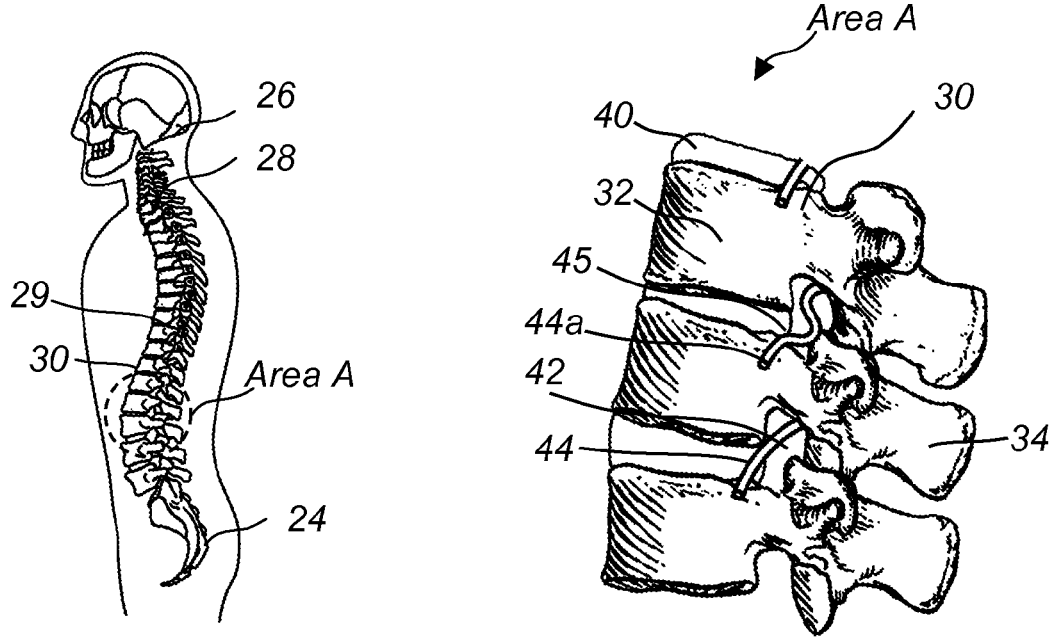
FIG. 1A
FIG. 1B
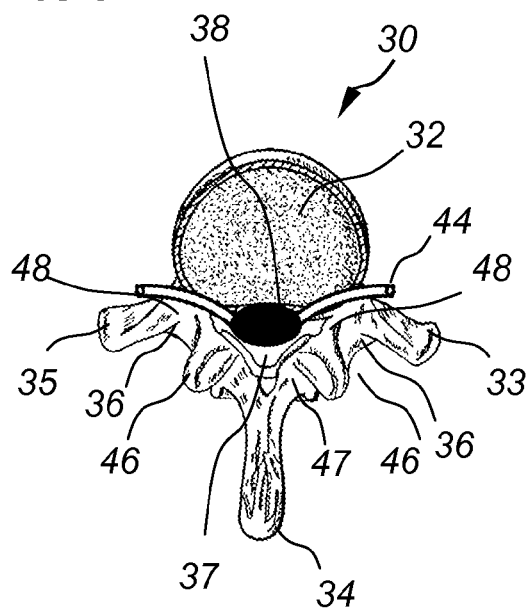
FIG. 1C

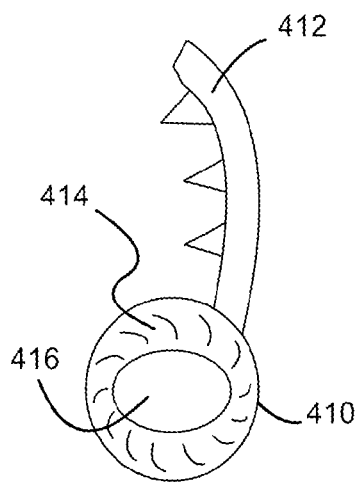
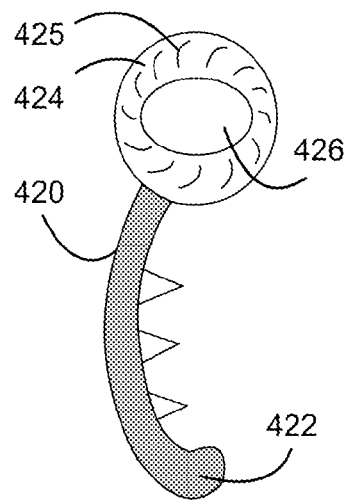
FIG. 25A                FIG. 25B
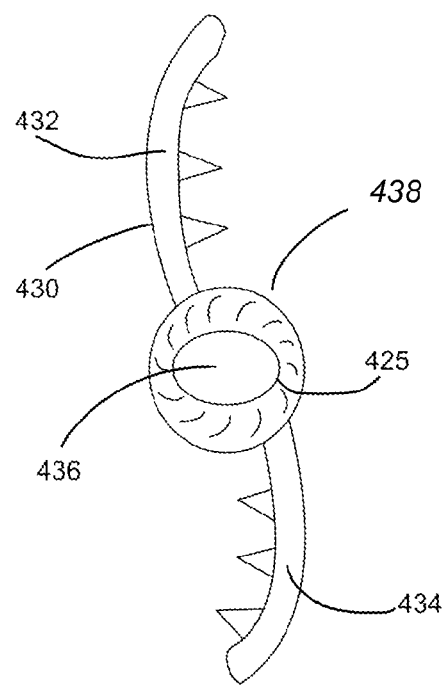
FIG. 25C

SPINOUS PROCESS FIXATION IMPLANT

CROSS REFERENCE TO RELATED CO-PENDING APPLICATIONS

This application claims the benefit of U.S. provisional application Ser. No. 60/750,520 filed Dec. 14, 2005 and entitled "SPINOUS PROCESS FIXATION IMPLANT", the contents of which are expressly incorporated herein by reference.

This application is also a continuation of U.S. application Ser. No. 11/609,418 filed on Dec. 12, 2006 and entitled SPINOUS PROCESS FIXATION IMPLANT the contents of which are expressly incorporated herein by reference.

FIELD OF THE INVENTION

The present invention relates to a system and a method for spinal stabilization through an implant, and more particularly to spinal stabilization through attachment of the implant to the spinous processes along one or more vertebras.

BACKGROUND OF THE INVENTION

The human spine comprises individual vertebras 30 (segments) that are connected to each other to form a spinal column 29, shown in FIG. 1. Referring to FIGS. 1B and 1C, each vertebra 30 has a cylindrical bony body (vertebral body) 32, three winglike projections (two transverse processes 33, 35 and one spinous process 34), left and right facet joints 46, lamina 47, left and right pedicles 48 and a bony arch (neural arch) 36. The bodies of the vertebrae 32 are stacked one on top of the other and form the strong but flexible spinal column. The neural arches 36 are positioned so that the space they enclose forms a tube, i.e., the spinal canal 37. The spinal canal 37 houses and protects the spinal cord and other neural elements. A fluid filled protective membrane, the dura 38, covers the contents of the spinal canal. The spinal column is flexible enough to allow the body to twist and bend, but sturdy enough to support and protect the spinal cord and the other neural elements. The vertebras 30 are separated and cushioned by thin pads of tough, resilient fiber known as inter-vertebral discs 40. Disorders of the spine occur when one or more of the individual vertebras 30 and/or the inter-vertebral discs 40 become abnormal either as a result of disease or injury. In these pathologic circumstances, fusion of adjacent vertebral segments may be tried to restore the function of the spine to normal, achieve stability, protect the neural structures, or to relief the patient of discomfort.

Several spinal fixation systems exist for stabilizing the spine so that bony fusion is achieved. The majority of these fixation systems utilize rods that attach to screws threaded into the vertebral bodies or the pedicles 48, shown in FIG. 3C. In some cases plate fixation systems are also used to fuse two adjacent vertebral segments. This construction usually consists of two longitudinal plates that are each placed laterally to connect two adjacent pedicles of the segments to be fused. This system can be extended along the sides of the spine by connecting two adjacent pedicles at a time similar to the concept of a bicycle chain. Current plate fixation systems are basically designed to function in place of rods with the advantage of allowing intersegmental fixation without the need to contour a long rod across multiple segments. Both the plating systems and the rod systems add bulk along the lateral aspect of the spine limits access to the pars and transverse processes for decortication and placement of bone graft. In order to avoid this limitation many surgeons decorticate before placing the rods, thereby increasing the amount of blood loss and making it more difficult to maintain a clear operative field. Placing rods or plates lateral to the spine leaves the center of the spinal canal that contains the dura, spinal cords and nerves completely exposed. In situations where problems develop at the junction above or below the fused segments necessitating additional fusion, the rod fixation system is difficult to extend to higher or lower levels that need to be fused. Although there are connectors and techniques to lengthen the fixation, they tend to be difficult to use and time consuming.

Accordingly, there is a need for a spinal stabilization device that does not add bulk to the lateral aspect of the spine and does not limit access to the pars and transverse processes for decortication and placement of bone graft.

SUMMARY OF THE INVENTION

In general, in one aspect, the invention features an implantable assembly for stabilization of spinous processes including a k-shaped component comprising an elongated plate and top and bottom deformable plates extending at first and second angles from a first surface of the elongated plate, respectively, thereby defining first and second spaces between the elongated plate and the top and bottom deformable plates and a compression element configured to compress and move the first and second deformable plates toward the elongated plate and to change the first and the second angles, respectively. The first and second spaces are configured to receive first and second spinous processes, respectively. Moving the first and second deformable plates toward the elongated plate results in engaging the first surface of the elongated plate and first surfaces of the top and bottom deformable plates with lateral surfaces of the first and second spinous processes, respectively.

Implementations of this aspect of the invention may include one or more of the following features. The compression element includes a plate placed on top of the top and bottom deformable plates and a bolt configured to pass through concentrically aligned through-bore openings formed in the center of the plate, the top and bottom deformable plates and the center of the elongated plate. The bolt comprises a head having a diameter larger that the diameter of the plate's through-bore and an elongated body having threads formed at a portion of the elongated body, the threads being dimensioned to engage inner threads in the elongated plate's through-bore. Tightening the bolt engages the bolt threads with the inner threads in the elongated plate's through-bore and compresses the head onto the plate and the plate onto the deformable top and bottom plates, causing them to move toward the elongated plate. The first surface of the elongated plate faces the first surfaces of the top and bottom deformable plates and all first surfaces comprise protrusions configured to engage and frictionally lock the elongated plate's first surface and the deformable top and bottom plates' first surfaces onto the lateral surfaces of the first and second spinous processes. The may be teeth, spikes, serrations, rough coatings or ridges. The assembly may further include a top locking member configured to lock the elongated plate's top end and the top deformable plate's top end. The top locking member includes a long bolt configured to be threaded through bolt holes formed through the top deformable plate's end, the first spinous process and the elongated plate's top end. The top locking member may be staples, cables, sutures, pins or screws. The assembly may further include a bottom locking member configured to lock the elongated plate's bottom end and the bottom deformable plate's bottom end. The bottom locking member comprises a long bolt configured to be threaded through bolt holes formed through the bottom deformable plate's bottom end, the second spinous process and the elongated plate's bottom end. The bottom locking member may be staples, cables, sutures, pins or screws. The elongated plate, the top and bottom deformable plates and the compression element may be made of stainless steel, titanium, gold, silver, alloys thereof, absorbable material, non-metal materials including synthetic ligament material, polyethylene, extensible materials or combinations thereof. The elongated plate and the top and bottom deformable plates may have adjustable lengths.

In general, in another aspect, the invention features a method for stabilizing spinous processes, including providing a k-shaped component having an elongated plate and top and bottom deformable plates extending at first and second angles from a first surface of the elongated plate, respectively, thereby defining first and second spaces between the elongated plate and the top and bottom deformable plates and a compression element configured to compresses and move the first and second deformable plates toward the elongated plate and to change said first and said second angles, respectively. Next, placing first and second spinous processes within the first and second spaces, respectively, and then compressing and moving the first and second deformable plates toward the elongated plate via the compression element, thereby engaging lateral surfaces of the first and second spinous processes onto the elongated plate's first surface and the first and second deformable plates' first surfaces, respectively.

Among the advantages of this invention may be one or more of the following. The assembly stabilizes vertebras by attaching plates to the spinous processes of the vertebras. This stabilization device does not add bulk to the lateral aspect of the spine and does not limit access to the pars and transverse processes for decortication and placement of bone graft.

The details of one or more embodiments of the invention are set forth in the accompanying drawings and description below. Other features, objects and advantages of the invention will be apparent from the following description of the preferred embodiments, the drawings and from the claims

BRIEF DESCRIPTION OF THE DRAWINGS

Referring to the figures, wherein like numerals represent like parts throughout the several views:

FIG. 1A is a side view of the human spinal column;
FIG. 1B is an enlarged view of area A of FIG. 1A;
FIG. 1C is an axial cross-sectional view of a lumbar vertebra;
FIG. 25A is a front side view of the front top pivoting component of the spinous process fixation implant of FIG. 24;
FIG. 25B is a front side view of the front bottom pivoting component of the spinous process fixation implant of FIG. 24;
FIG. 25C is a front side view of the back pivoting component of the spinous process fixation implant of FIG. 24.

DETAILED DESCRIPTION OF THE INVENTION

The present invention relates to a system and a method for a spinous process fixation implant.

Figure 2:
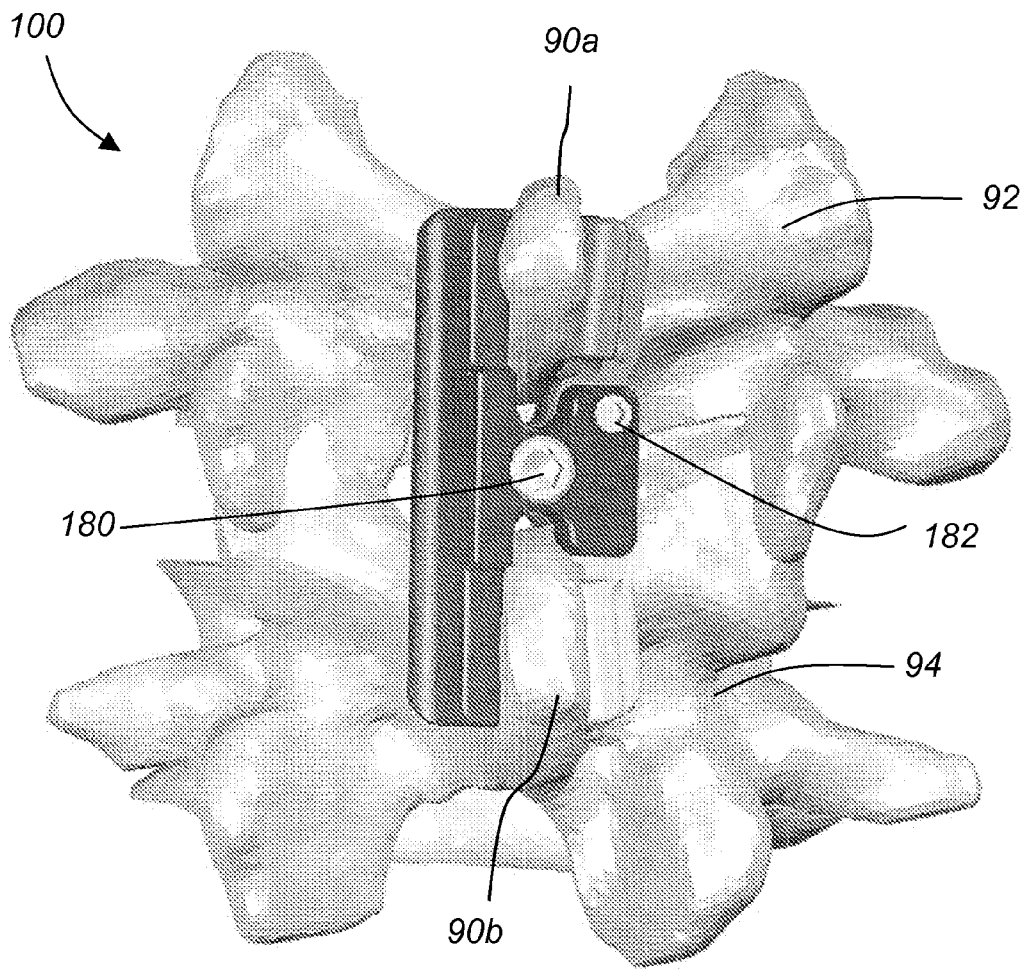
FIG. 2 is a posterior view of a portion of the spine with a first embodiment of a spinous process fixation implant according to the present invention affixed thereto.
Figure 3:
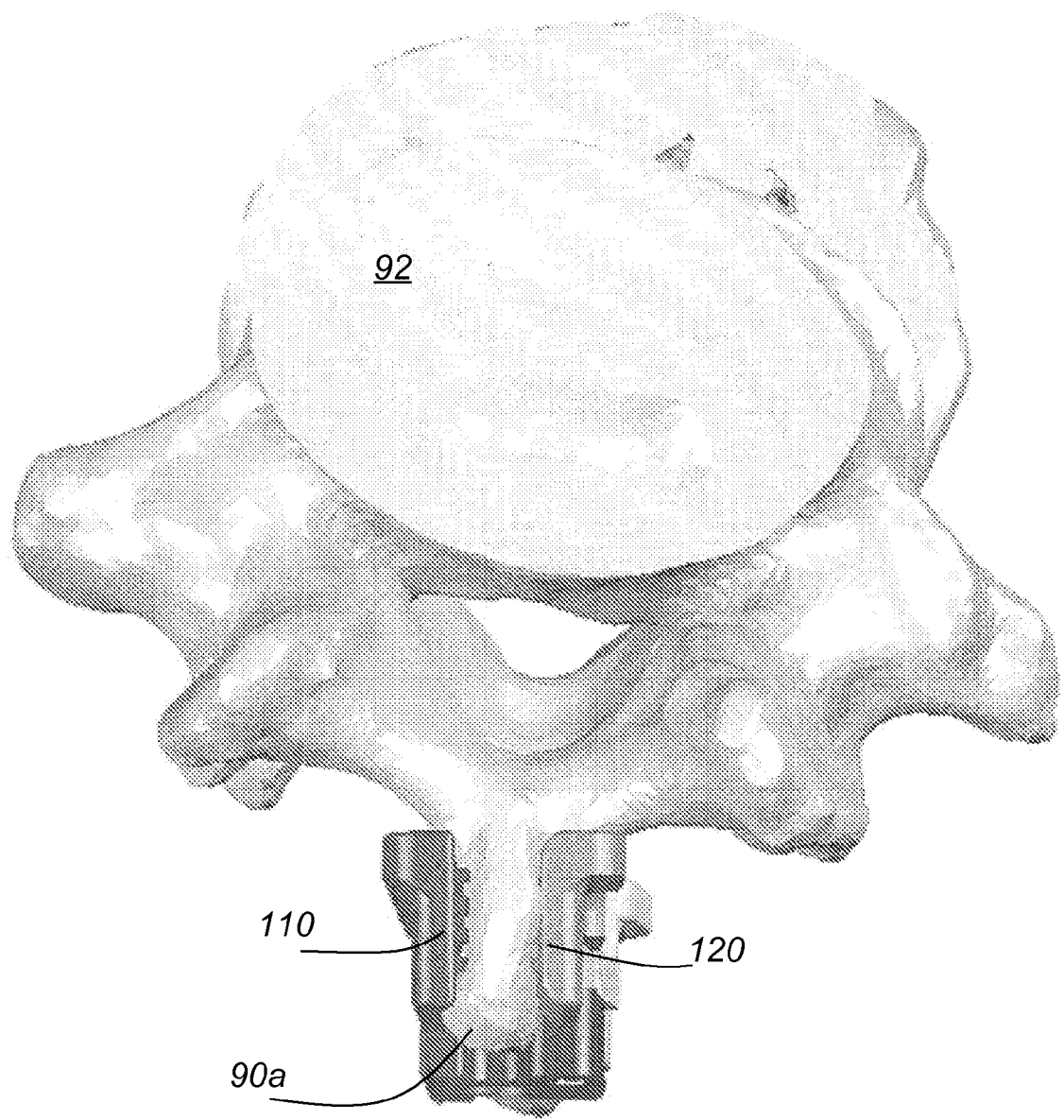
FIG. 3 is a top view of the spine with the spinous process fixation implant of FIG. 2 affixed thereto.
Figure 4:
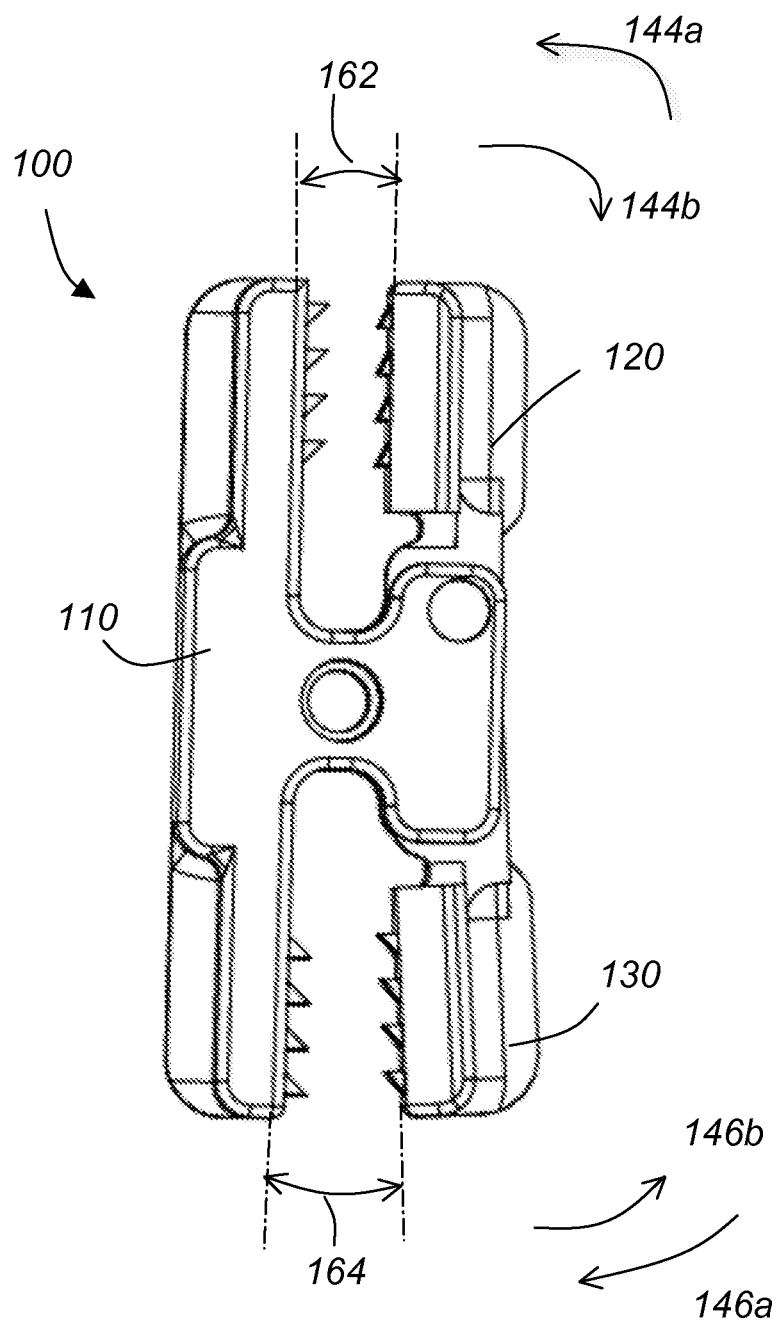
FIG. 4 is a front side view of the spinous process fixation implant of FIG. 2.
Figure 5:
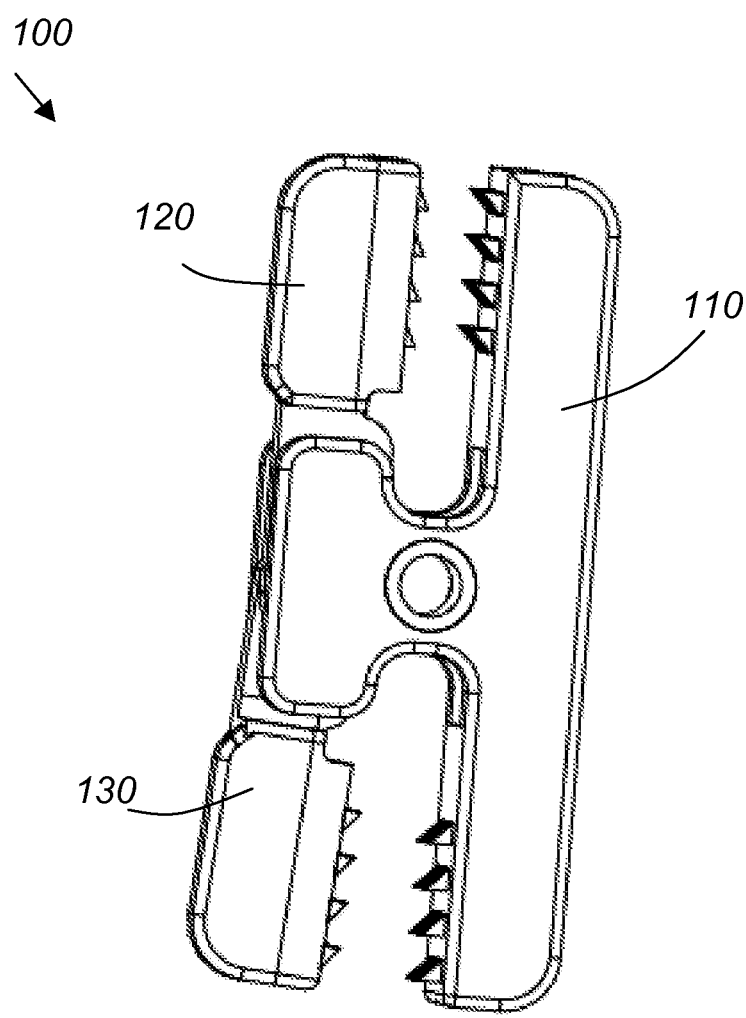
FIG. 5 is a back side view of the spinous process fixation implant of FIG. 2.
Figure 6:
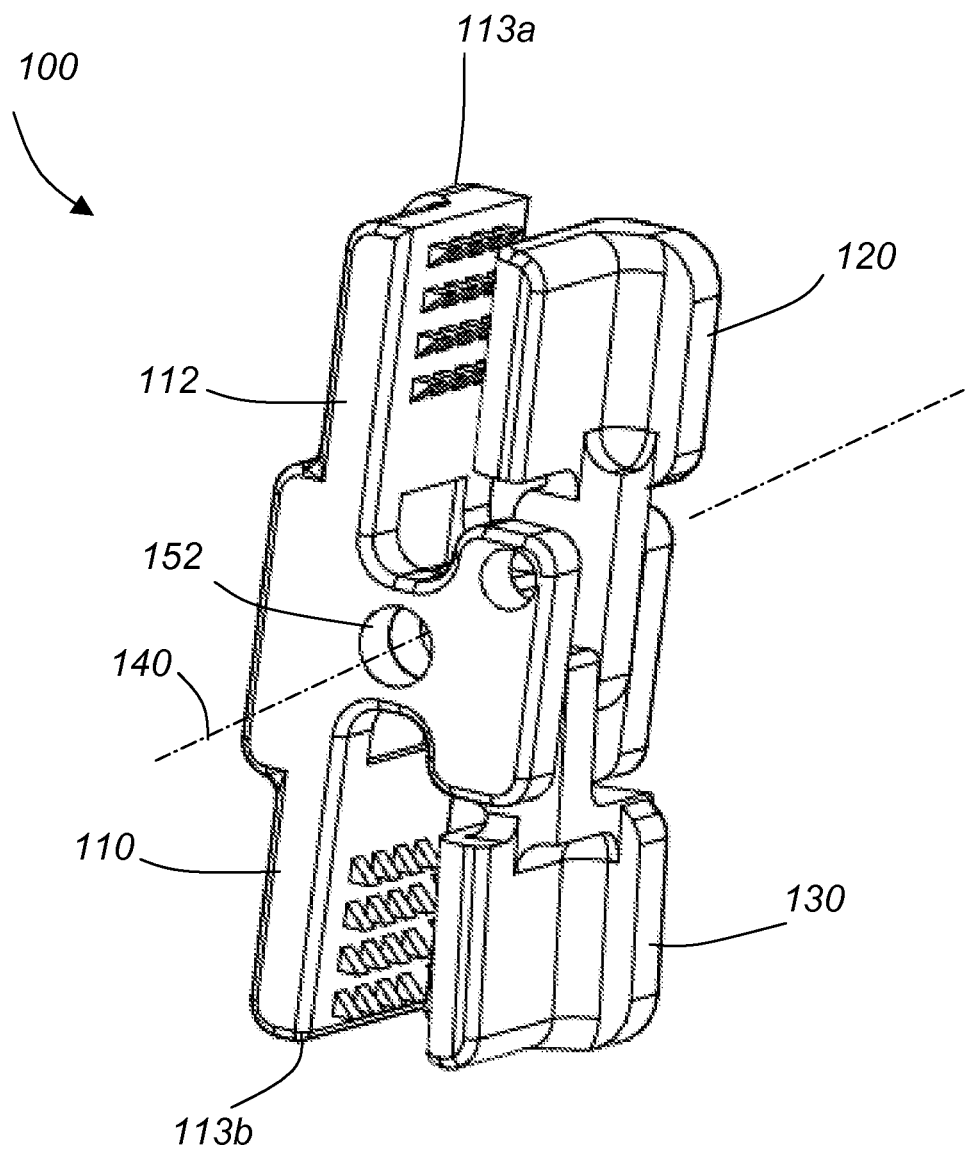
FIG. 6 is a right side perspective view of the spinous process fixation implant of FIG. 2.
Figure 10:
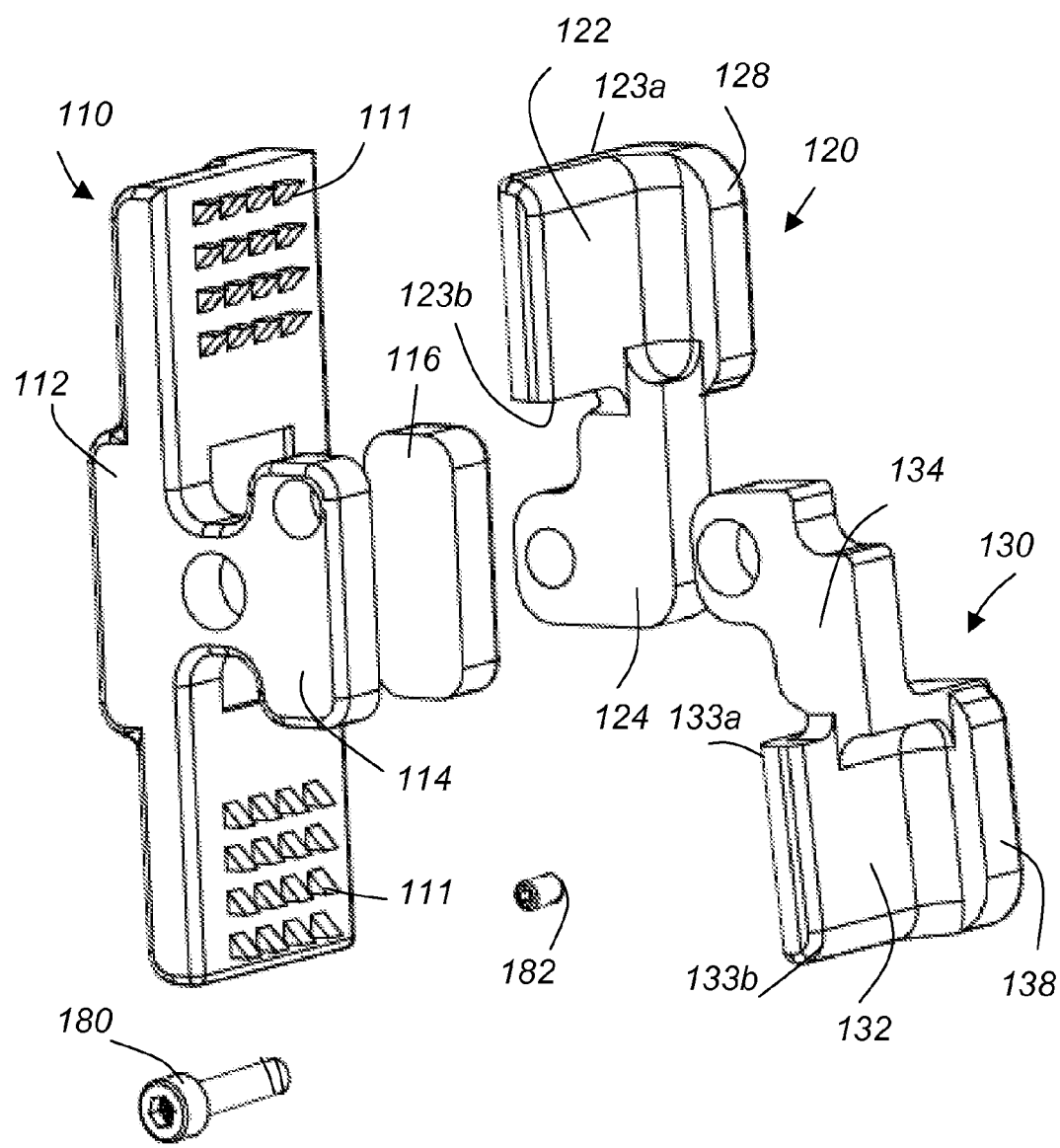
FIG. 10 is an exploded right side perspective view of the spinous process fixation implant of FIG. 2.
Figure 11:
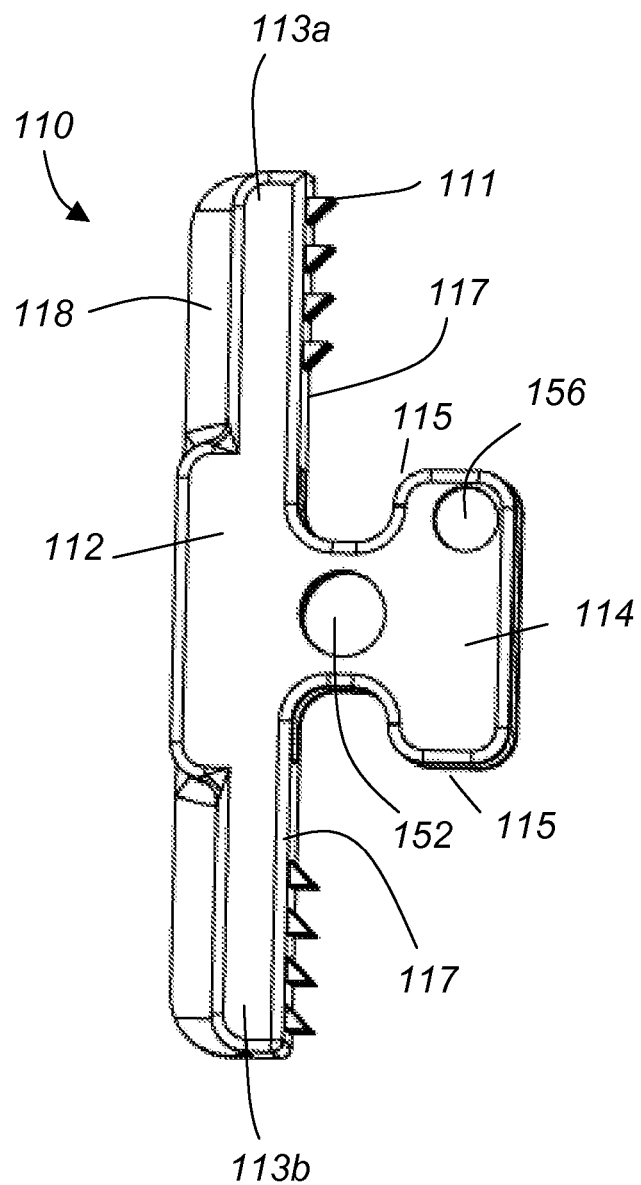
FIG. 11 is a front side view of the elongated component 110 of FIG. 2.
Figure 12:
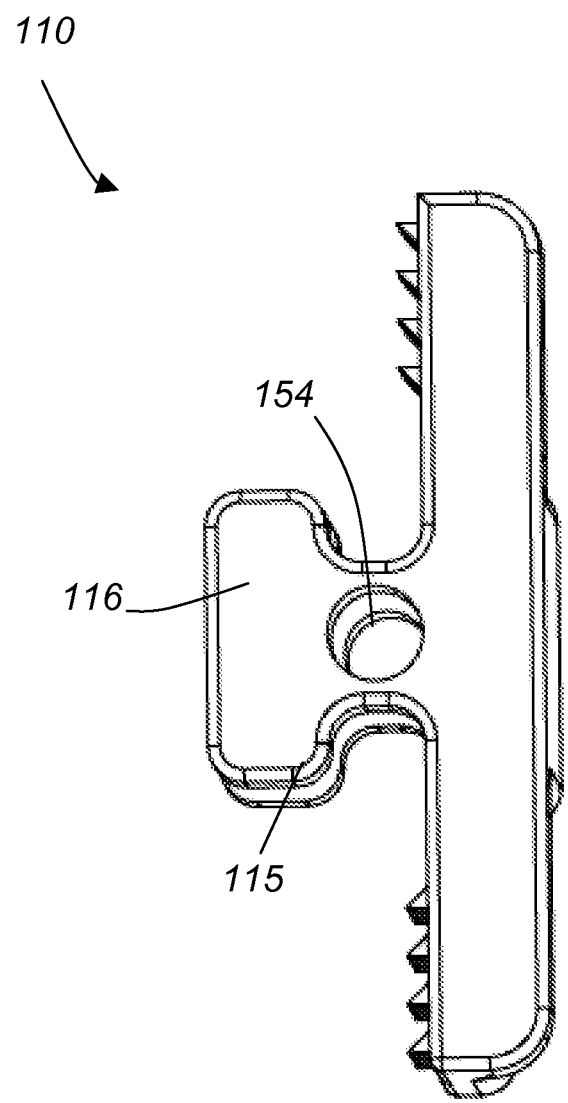
FIG. 12 is a back side view of the elongated component of FIG. 2.

Referring to FIG. 2, FIG. 3, and FIG. 4, a spinous process fixation assembly 100 stabilizes two adjacent vertebras 92, 94 of the human spine by engaging and locking their spinous processes 90a and 90b, respectively. Spinous process fixation assembly 100 includes an elongate plate 110 and top and a bottom pivoting plates 120, 130, located opposite to plate 110 and configured to form a K-shaped structure together with plate 110. Top and bottom pivoting plates 120, 130 pivot around axis 140 (shown in FIG. 6) independent from each other, forming angles 162, 164 with plate 110, respectively. The pivoting motion of plates 120, 130 along directions 144a, 144b and 146a, 146b, moves them close to or away from the elongated plate 110, as shown in FIG. 4. Elongated plate 110 has a body 112 and front and back cross plates 114, 116, extending at right angle to the front of the body 112 and back of the body 112, respectively, as shown in FIG. 10, FIG. 11 and FIG. 12. Body 112 has a top end 113a, a bottom end 113b, an outer surface 118 and an inner surface 117. Axis 140 passes through apertures 152 and 154 formed in the centers of the cross plates 114, 116, respectively, as shown in FIG. 11 and FIG. 12. Cross plates 114, 116 extend between the bottom surface and top surface of the adjacent spinous processes 90a, 90b, respectively and have edges 115 which are rounded and sculpted to correspond to the geometry of the spinous processes 90a, 90b and lamina around which they will fit once implanted. Cross plates 114, 116 are substantially flat, parallel to each other and a gap is formed between them sized to hold portions of the top and bottom pivoting plates 120, 130, as shown in FIG. 7.

Figure 13:
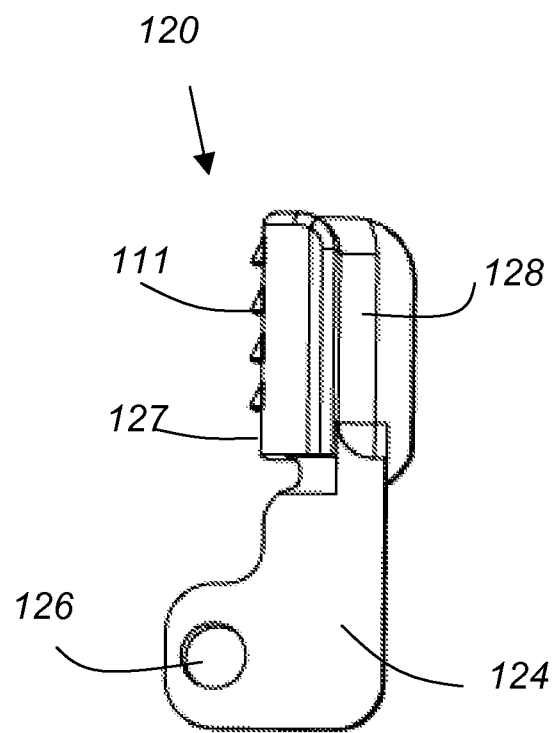
FIG. 13 is a front side view of the top pivoting component of FIG. 2.
Figure 14:
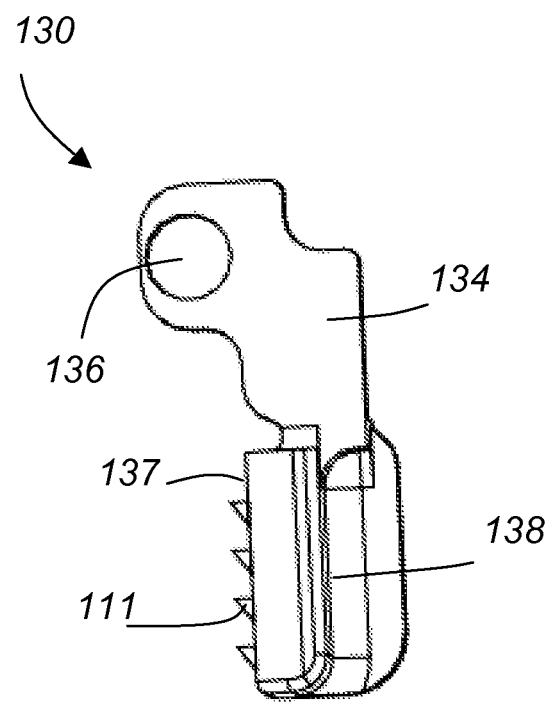
FIG. 14 is a front side view of the bottom pivoting component of FIG. 2.
Figure 15:
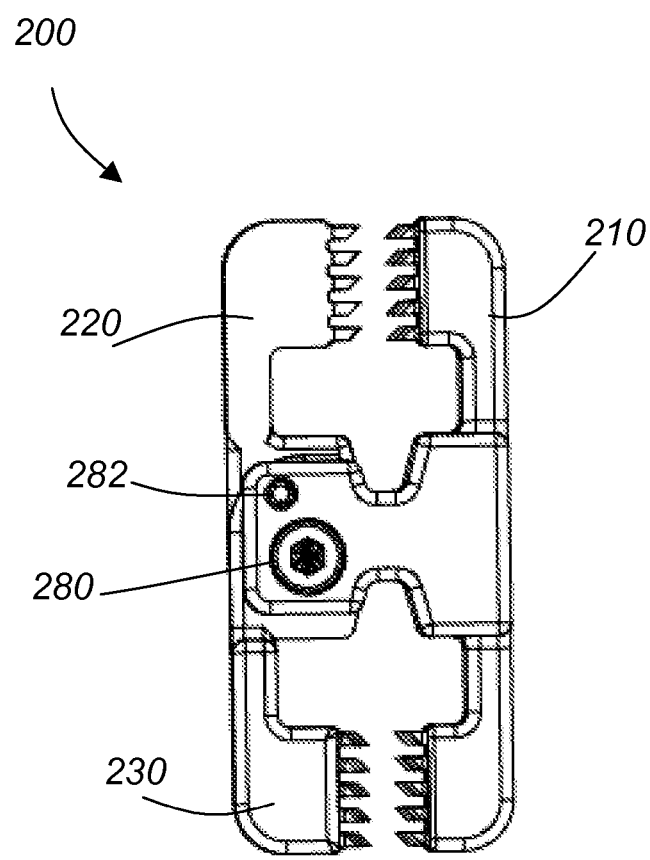
FIG. 15 is a front side view of a second embodiment of a spinous process fixation implant according to the present invention, depicting the top and bottom pivoting components in the closed position.
Figure 16:
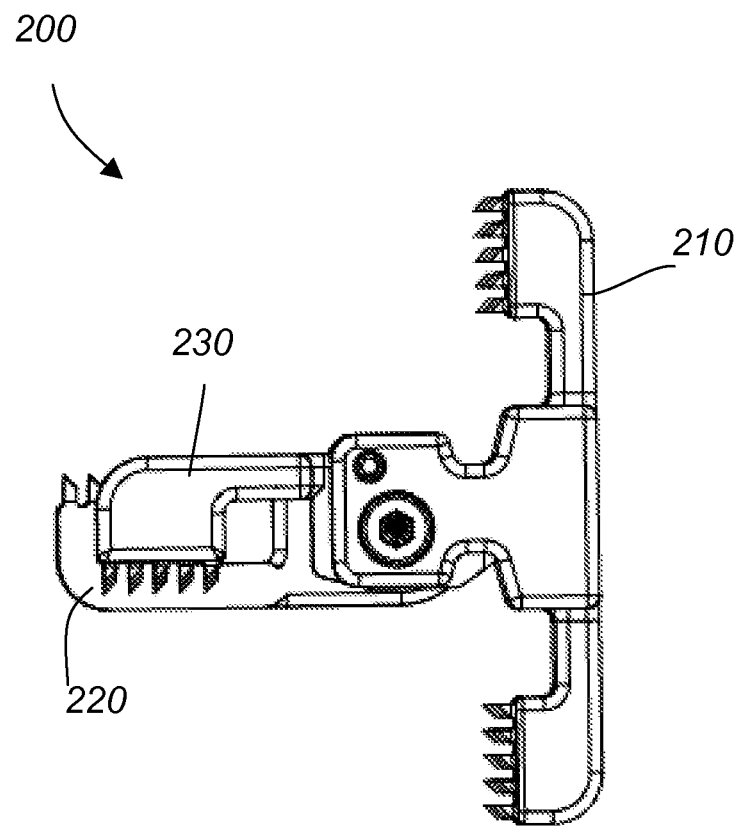
FIG. 16 is a front side view of the spinous process fixation implant of FIG. 15 with the top and bottom pivoting components in the open position.
Figure 17:
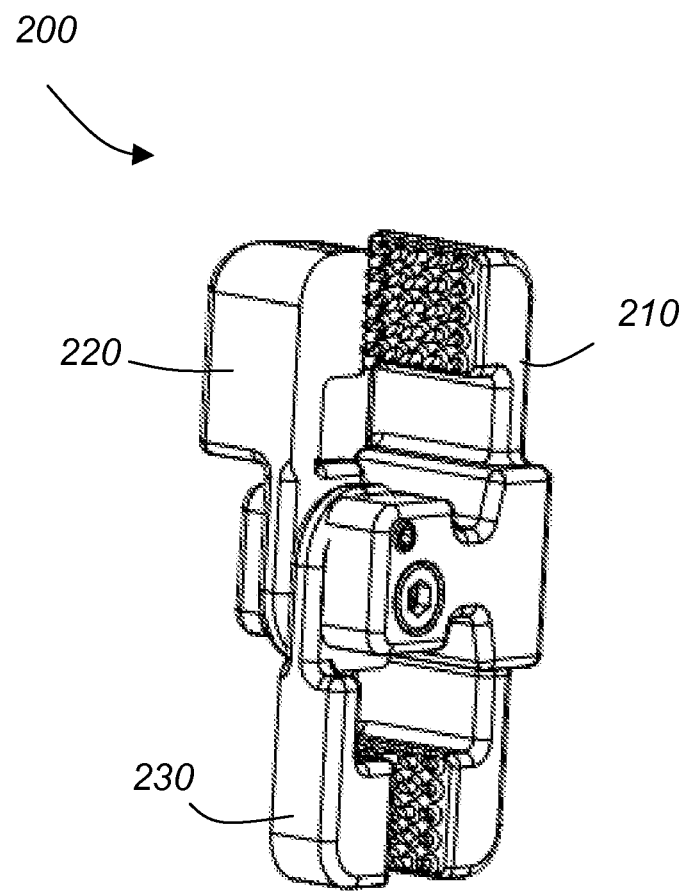
FIG. 17 is a left side perspective view of the spinous process fixation implant of FIG. 15, depicting the top and bottom pivoting components in the closed position.

Referring to FIG. 10, FIG. 13 and FIG. 14, top pivoting plate 120 has a main body 122 with top and bottom ends 123a, 123b, respectively and inner 127 and outer surface 128, respectively. An arm 124 extends downward from the bottom end 123b of the body 122 and a side plate 128 extends at right angle to the back of the body 122. The arm 124 has an aperture 126 located at the bottom left corner and extends from the front side to the back side of the arm 124. Similarly, bottom pivoting plate 130 has a main body 132 with top and bottom ends 133a, 133b, respectively, and inner and outer surfaces 137, 138 respectively. An arm 134 extends upward form the top end 133a and has an aperture 136 at the top left corner, extending from the front side to the back side of the arm 134, as shown in FIG. 10, and FIG. 14. A side plate 138 extends at right angle from to the back of the body 132. All edges of plates 110, 120, 130 are rounded to prevent damage of the adjacent tissue during implantation or spinal movement. Plates 110, 120, 130 are made of stainless steel, titanium, gold, silver, alloys thereof, absorbable material, non-metal materials including synthetic ligament material, polyethylene, extensible materials or combinations thereof. Plates 110, 120, 130 may have adjustable lengths. In one example plates 110, 120, 130 have lengths of 30 mm, 15 mm, 15 mm, respectively, and the assembly may have a width between 3 mm to 10 mm.

Figure 7:
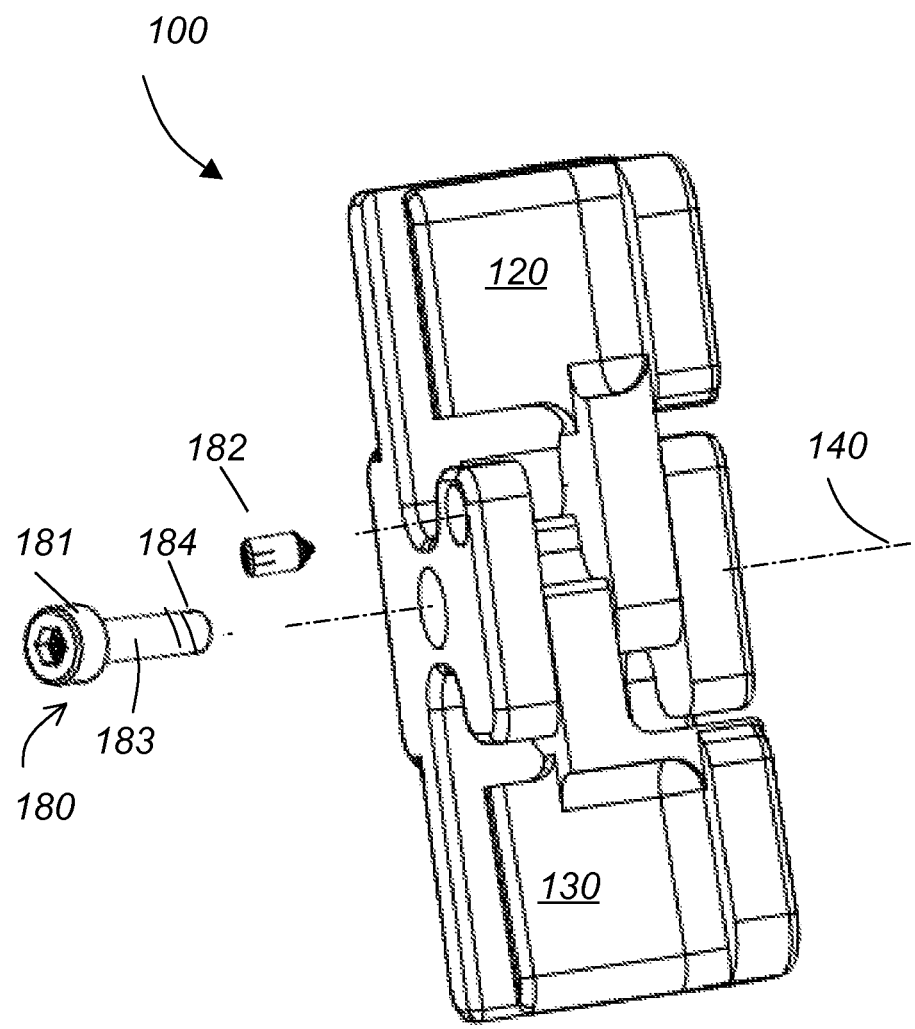
FIG. 7 is partially exploded right side perspective view of the spinous process implant of FIG. 2.
Figure 8:
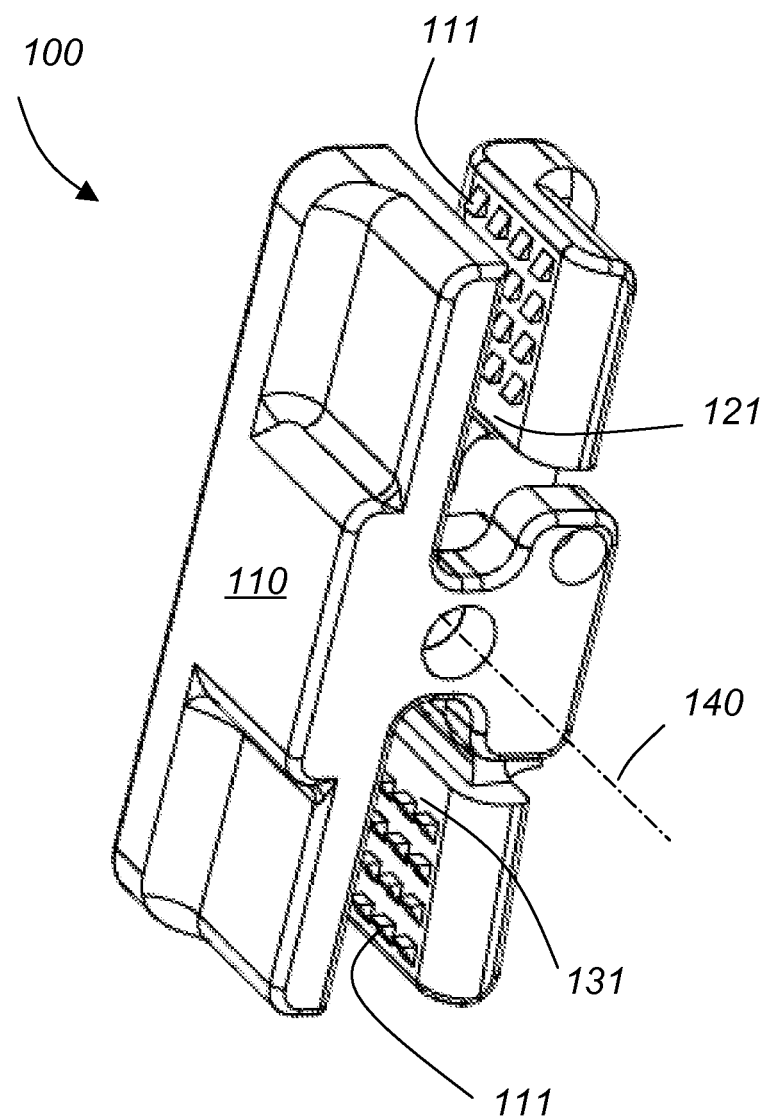
FIG. 8 is a left side perspective view of the spinous process fixation implant of FIG. 2.
Figure 9:
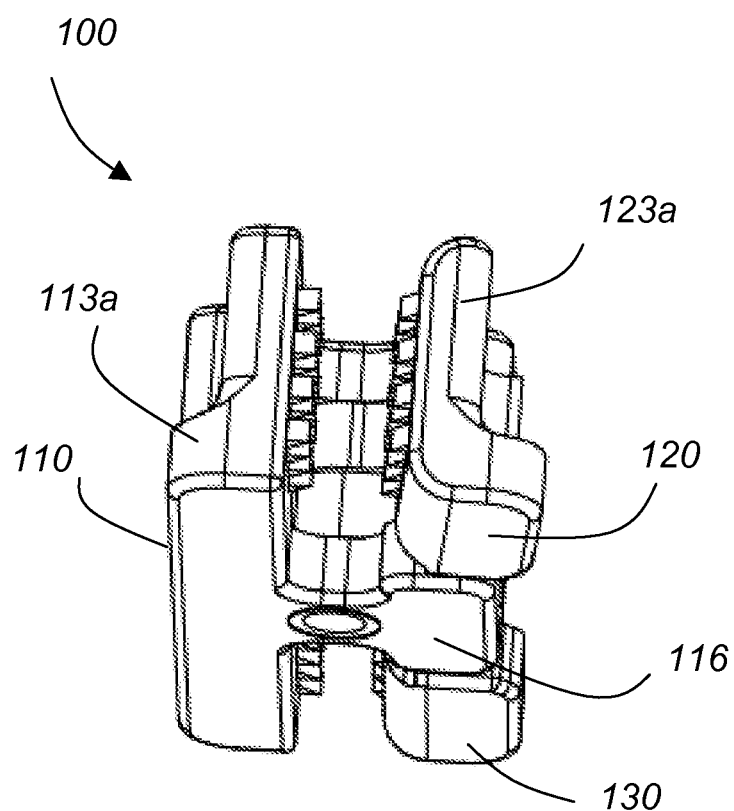
FIG. 9 is a top perspective view of the spinous process fixation implant of FIG. 2.

Referring to FIG. 7, a long bolt 180 passes through apertures 152 and 154 of the cross plates 114, 116 of the elongated plate 110 and though apertures 126 and 136 formed in the top and bottom pivoting plates 120, 130, respectively. Bolt 180 has a head 181, a shaft 183 and threads 184 formed on the end portion of the shaft 183. Threads 184 engage threads in the aperture 154 of the back cross plate 116, in order to hold and secure the three components 110, 120, 130, of the assembly 100 together. In other embodiments, a nut (not shown) is attached at the end of the bolt 180 to hold and secure the three components 110, 120, 130, of the assembly 100 together. In other embodiments bolt 180 is threaded into the cartilage between the two vertebras to secure the three components 110, 120, 130 together and to attach the assembly 100 onto the spine. The inner surfaces 117, 127, 137 of plates 110, 120, 130, respectively, have protrusions 111 that grab and frictionally engage the sides of the spinous processes 90a, 90b, as shown in FIG. 3, FIG. 11, FIG. 13 and FIG. 14. Protrusions 111 may be teeth, serrations, ridges, and other forms of rough surfaces or coatings that produce rough surfaces. The position of pivoting plates 120, 130 relative to each other and relative to plate 110 is locked with a set screw 182 passing trough the aperture 156 formed in the upper right corner of the front cross plate 114. Tightening of the setscrew 182 locks the front and back cross plates 114, 116 to the pivoting plates 120 and 130. Engaging and locking the spinous process fixation assembly 100 onto spinous processes 90a, 90b, prevents the components 110, 120 and 130 from moving sidewise or up and down toward or away from each other during spinal movement.

The assembled spinous process fixation assembly 100 is implanted into the patient with the use of instrumentation (not shown) between the two adjacent spinous processes 90a, 90b, as shown in FIG. 2. The cross plates 114, 116 are placed between the spinous processes 90a, 90b so that the body 112 of the elongated plate 110 and the top and bottom pivoting plates 120, 130 fall on the lateral sides of the spinous processes 90a, 90b. One spinous process 90a lies between the top portion of the body 112 and the top pivoting plate 120, as shown in FIG. 3, and the other spinous process 90b lies between the bottom portion of the body 112 and the bottom pivoting plate 130, with their inner surfaces 117, 127, 137 facing the lateral surfaces of the spinous processes 90a, 90b. On each of the inner surfaces 117, 127, 137 of the plates 110, 120, 130, respectively, the protrusions 111 face toward the lateral surface of the adjacent spinous process. At this point, the top and bottom pivoting plates 120, 130 are pivoted as necessary to provide the desired fit of the plates to the spinous processes. The bolt 180 is tightened, clamping the protrusions 111 into the surfaces of the spinous processes and locking the three plates relative to each other by engaging the threads of the aperture 154. The protrusions 111 and the threading of the bolt into aperture 154 of the back cross plate 116 frictionally secures the spinous process fixation assembly 100 onto the spinous processes 90a, 90b and helps prevent the device from shifting or slipping.

Referring to FIG. 15, FIG. 16, FIG. 17, FIG. 18, in a second embodiment of the spinous process fixation assembly 200, the top and bottom pivoting plates 220, 230 are designed to pivot past each other and to form any angle with the elongated plate 210 between 0 and 180 degrees. In particular, plates 220 and 230 pivot to a 90 degree angle relative to plate 210 and form a sidewise oriented T, shown in FIG. 16 and FIG. 180. The assembly 200 of FIG. 16, with the pivoting plates 220, 230 at a 90 degree angle with the plate 110, is inserted sidewise between the top and bottom spinous processes 90a, 90b. Once the assembly is inserted, the plates 220 and 230 are pivoted upward and downward, respectively, and are placed at angles relative to the plate 210 necessary to provide the desired fit of the plates to the spinous processes. Sidewise implantation of the assembly 200 has the advantage of reduced trauma in the area between the spinous processes.

Figure 19:
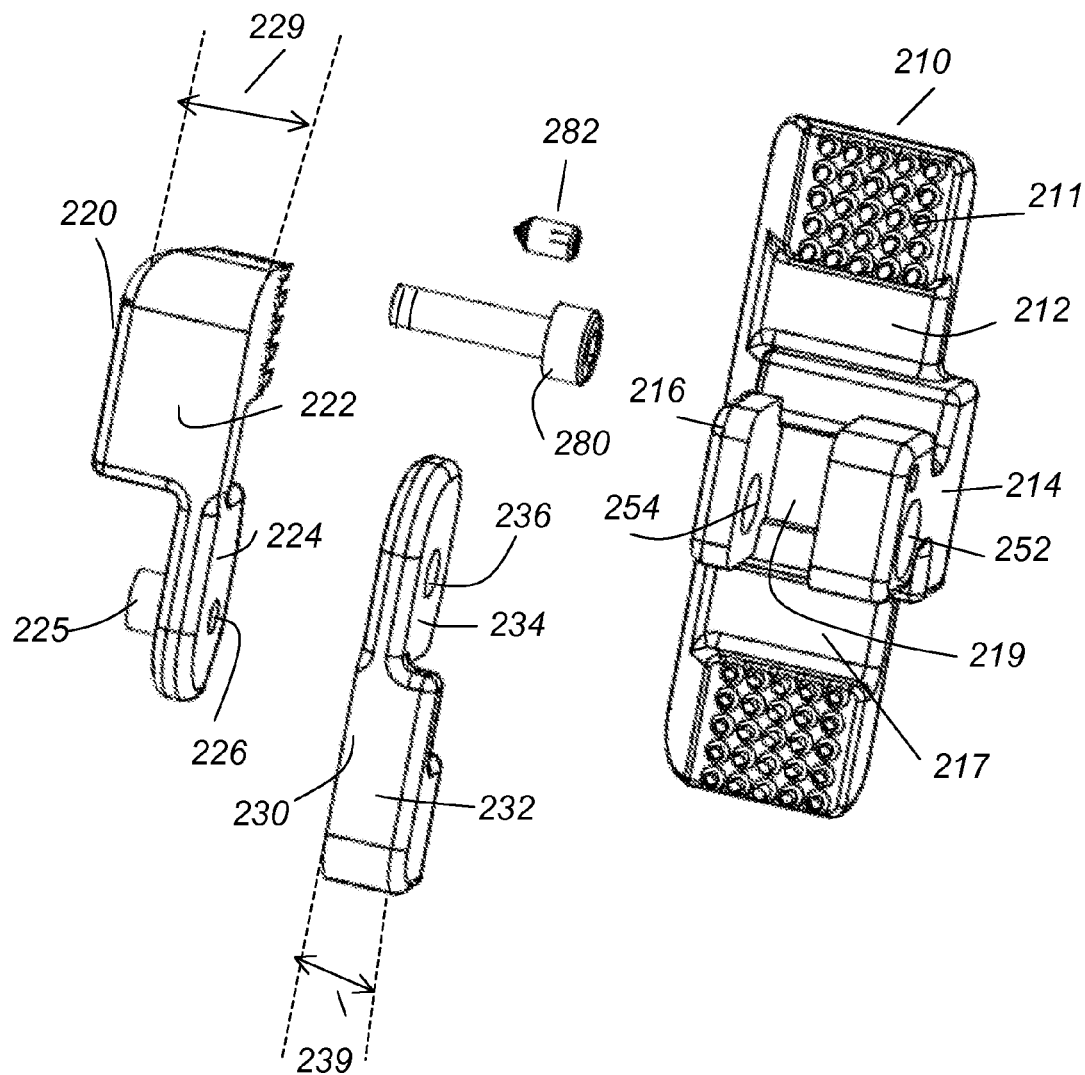
FIG. 19 is an exploded left side view of the spinous process fixation implant of FIG. 15.
Figure 20A:
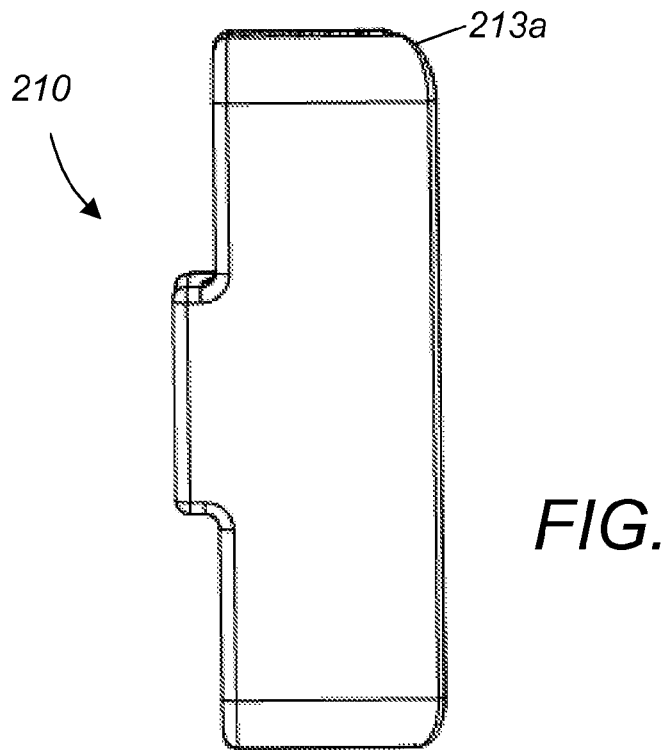
FIG. 20A is a right side view of the elongated plate component 210 of FIG. 15.
Figure 20B:
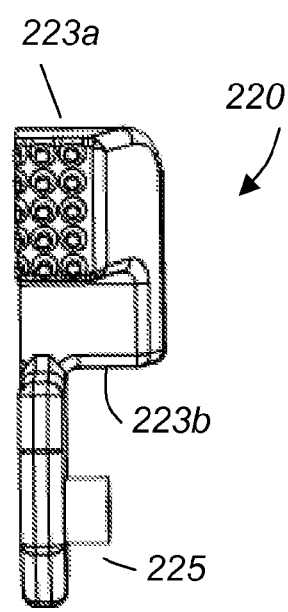
FIG. 20B is a right side view of the top pivoting component 220 of FIG. 15.
Figure 20C:
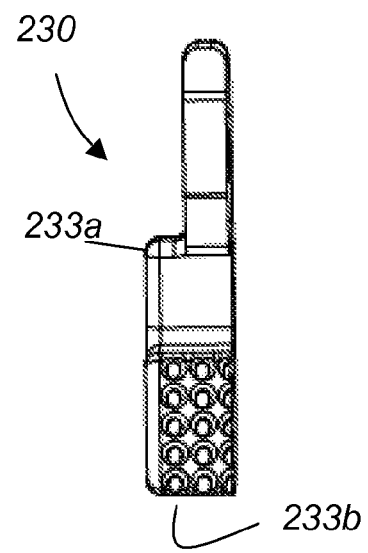
FIG. 20C is a right side view of the bottom pivoting component 230 of FIG. 15.

In this embodiment the top pivoting plate 220 has a main body 222 with top and bottom ends 223a, 223b, respectively and inner 227 and outer surface 228, respectively, shown in FIG. 19, FIG. 20. Main body 222 has a width 229 dimensioned to allow plate 220 to pivot past plate 230 when placed in the gap 219 between the two cross plates 214, 216 of plate 210. An arm 224 extends downward from the bottom end 223b of the body 222. The arm 224 has an aperture 226 located at the center of the bottom end of the arm and extends from the front side to the back side of the arm 224. A protruding annulus 225 surrounds aperture 226 and projects outward form the back side of the arm 224. Annulus 225 is dimensioned to fit within aperture 254 of the back cross plate 216. Aperture 226 includes inner threads (not shown) extending from the front to the back side of the arm 224. Similarly, bottom pivoting plate 230 has a main body 232 with top and bottom ends 233a, 233b, respectively, and inner and outer surfaces 237, 238 respectively. Main body 232 has a width 239 dimensioned to allow plate 230 to pivot past plate 220 when placed in the gap 219 between the two cross plates 214, 216 of plate 210. An arm 234 extends upward form the top end 233a and has an aperture 236 located at the center of the top end of the arm and extends from the front side to the back side of the arm 234, as shown in FIG. 19 and FIG. 20C.

Figure 18:
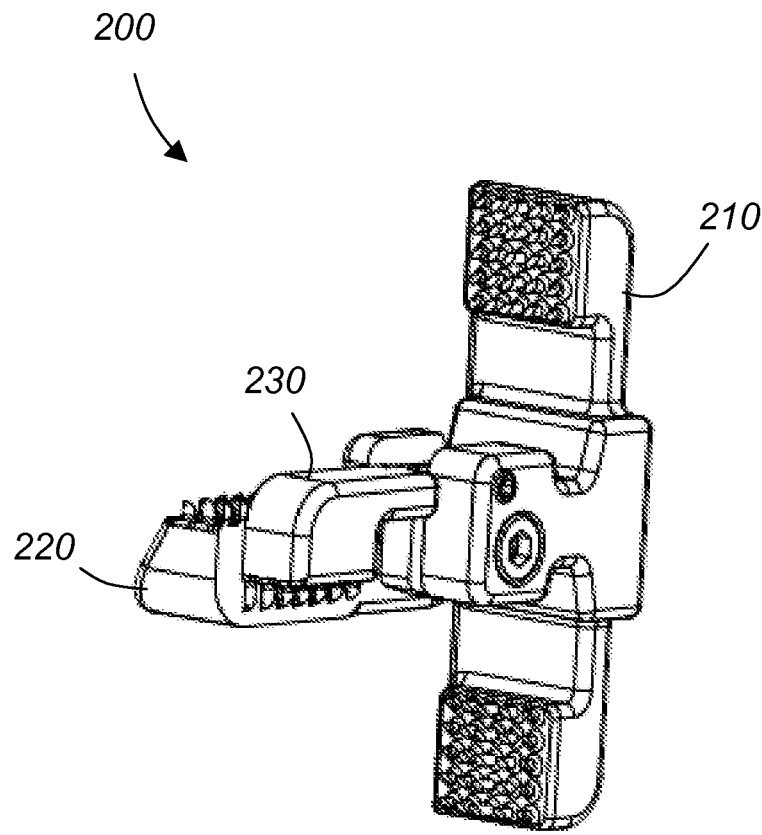
FIG. 18 is a left side perspective view of the spinous process fixation implant of FIG. 15, depicting the top and bottom pivoting components in the open position.

Elongated plate 210, top pivoting plate 220 and bottom pivoting plate 230 are assembled together, as shown in FIG. 18. Annulus 225 is inserted in the aperture 254 of the back cross plate 216 and the apertures 252, 236, 226 of the front cross plate 214, bottom pivoting plate 230 and top pivoting plate 220, respectively, are aligned. A long bolt 280 is inserted through the aligned apertures and threaded in the inner threads of the aperture 226. The position of pivoting plates 220, 230 relative to each other and relative to plate 210 is locked with a set screw 282 passing trough the aperture 256 formed in the upper left corner of the front cross plate 214. Tightening of the set screw 282 locks the front and back cross plates 214, 216 to the pivoting plates 220 and 230. Once assembly 200 is implanted into the patient between the two adjacent spinous processes 90a, 90b, the assembly is secured and locked in position, according to the process described above.

Figure 21:
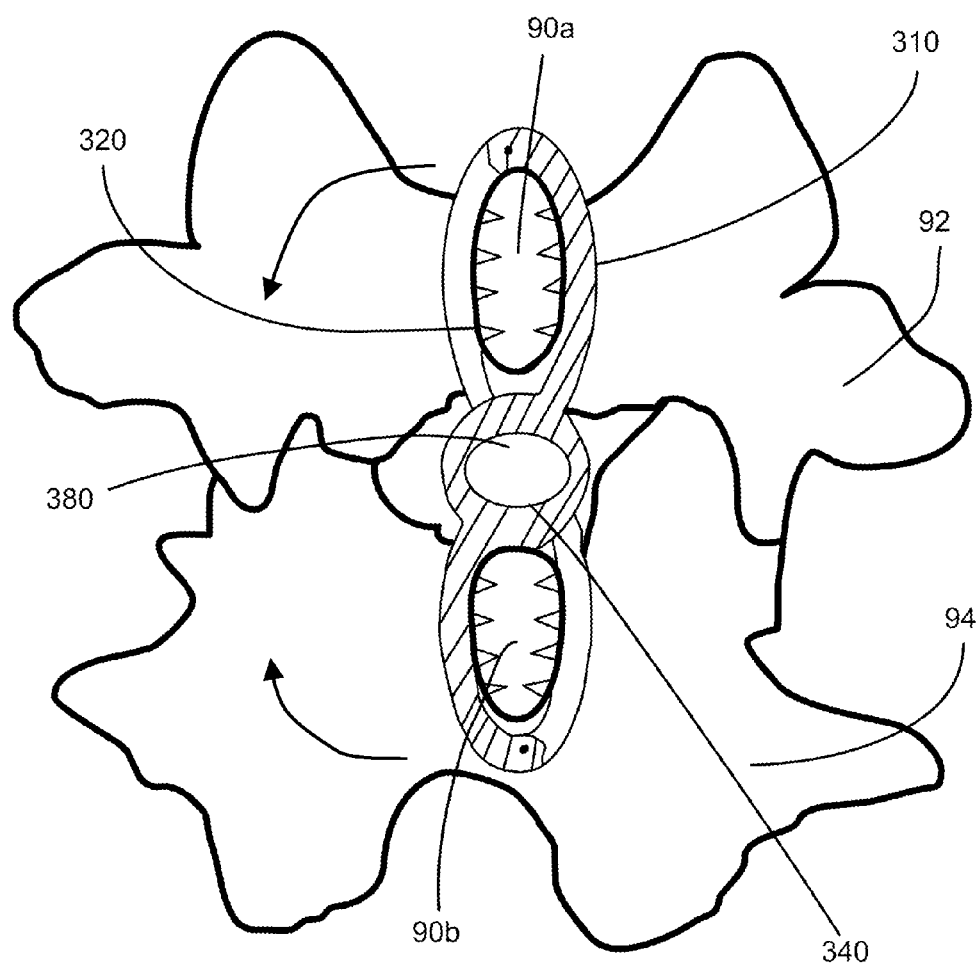
FIG. 21 is a front side view of a third embodiment of a spinous process fixation implant according to the present invention, depicting front and back pivoting components in the closed position around the spinous processes.

Referring to FIG. 21, in a third embodiment the spinous process fixation assembly 300 includes a front S-shaped plate 310 and a mirror image back S-shaped plate 320 connected at their centers via a bolt 380 forming an X-shaped structure. The front S-shaped plate 310 pivots relative to a back S-shaped plate 320 around pivot point 340 and the spinous process 90a of the top vertebra 92 is frictionally engaged between the upper arms of S-plates 310 and 320, while the spinous process 90b of the bottom vertebra 42 is frictionally engaged between the lower arms of S-plates 310 and 320. A bolt 380 is threaded through apertures formed in the centers of the front and back S-plates, as shown in FIG. 21. The inner surfaces of the upper and lower arms of the S-shaped plates are sculpted to fit the shape of the spinous processes and have protrusions that frictionally engage the sides of the spinous processes and together with the bolt 380 securely lock the assembly 300 between the spinous processes 90a, 90b.

Figure 22A:
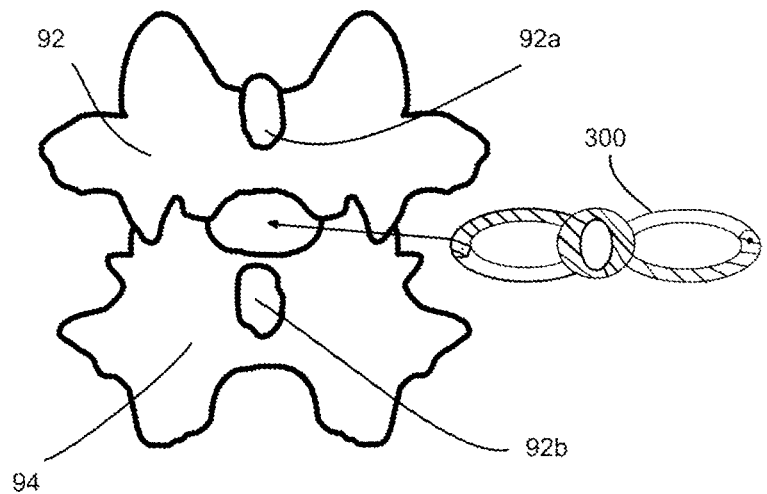
FIG. 22A depicts insertion of the spinous process fixation implant of FIG. 21 from the side with front and back pivoting components in the open position.
Figure 22B:
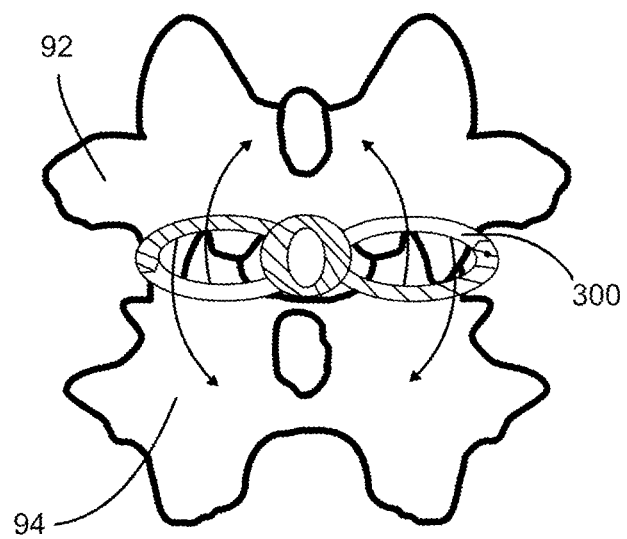
FIG. 22B depicts pivoting the front and back pivoting components of FIG. 21 to close them around the spinous processes.
Figure 23:
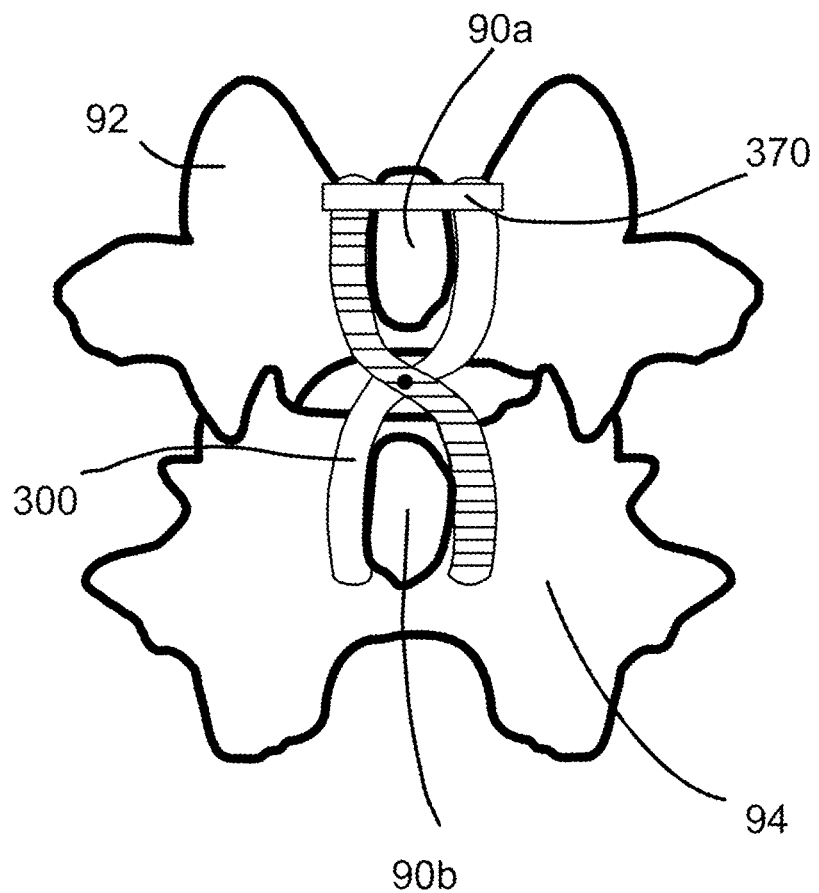
FIG. 23 is a front side view of the embodiment of a spinous process fixation implant according of FIG. 21, depicting front and back pivoting components in the closed position and locked position around the spinous processes.

Assembly 300, with the S-shaped plates 310, 320 assembled and oriented horizontally, as shown in FIG. 22A, is inserted sidewise between the top and bottom spinous processes 90a, 90b. Once the assembly is inserted, plates 310 and 320 are pivoted upward and downward, respectively, as shown in FIG. 22B, and they assume a vertical orientation so that their corresponding inner surfaces surround spinous processes 90a, 90b. Sidewise implantation of the assembly 300 has the advantage of reduced trauma in the area between the spinous processes.

Long bolts 370 may be added to this embodiment to further anchor the assembly 300 on the spinous processes. If they are added, appropriately sized holes must be drilled laterally through the spinous processes prior to placement of the device. Once the device is in place as described above, one long bolt 370 is threaded through a bolt hole on the top end of plate 310, through the drilled hole in the spinous process 90a, then out through a bolt hole on top end of plate 320. A second long bolt 370 may also be threaded through a bolt hole on the bottom end of plate 310, through the drilled hole in the spinous process 90b, then out through a bolt hole on the bottom end of plate 320. Tightening of bolts 380 and 370 securely locks the assembly 300 around spinous processes 90a, 90b.

Figure 24:
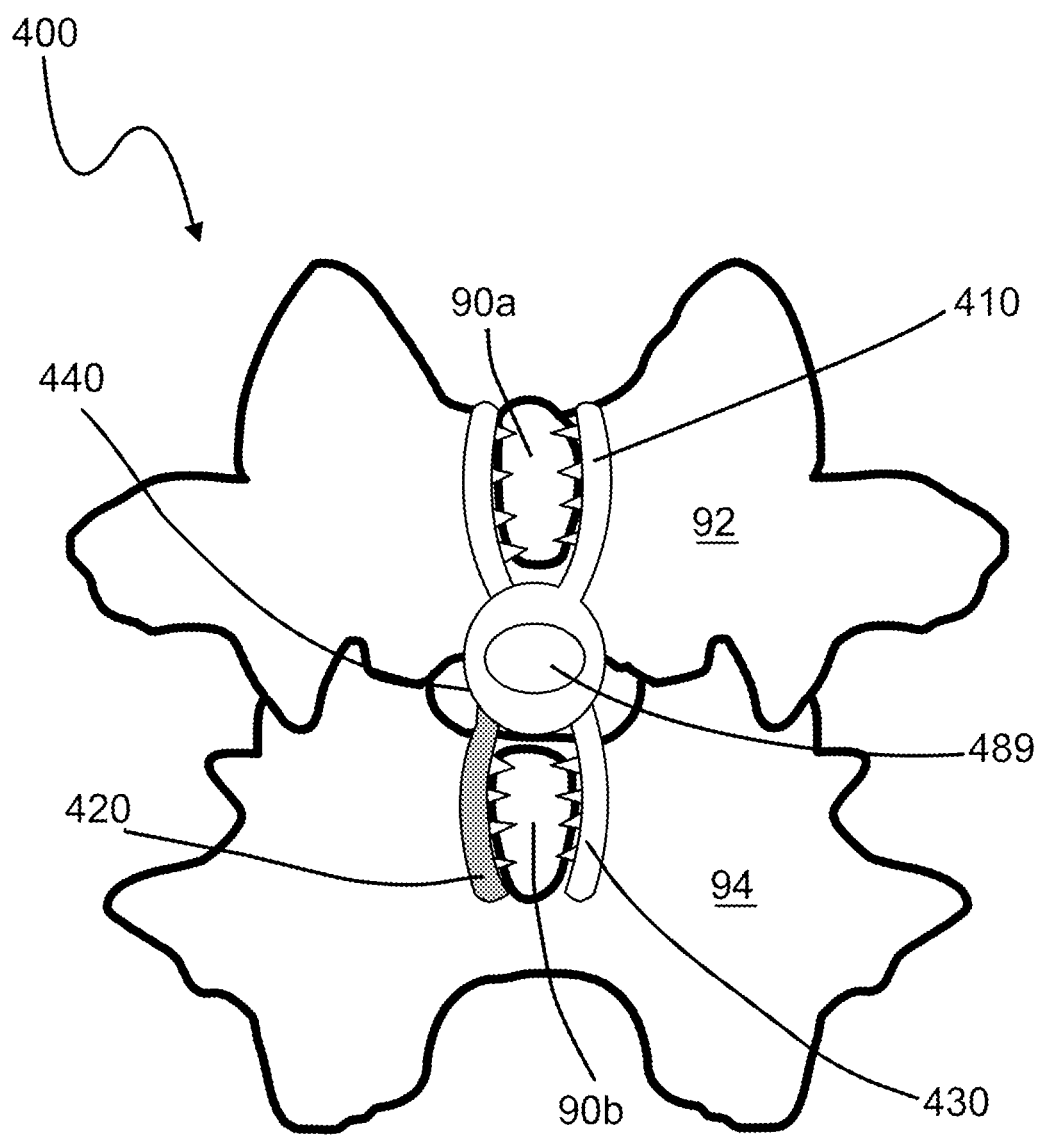
FIG. 24 is a front side view of a fourth embodiment of a spinous process fixation implant according to the present invention, depicting front top, front bottom and back pivoting components in the closed position around the spinous processes.
Figure 26:
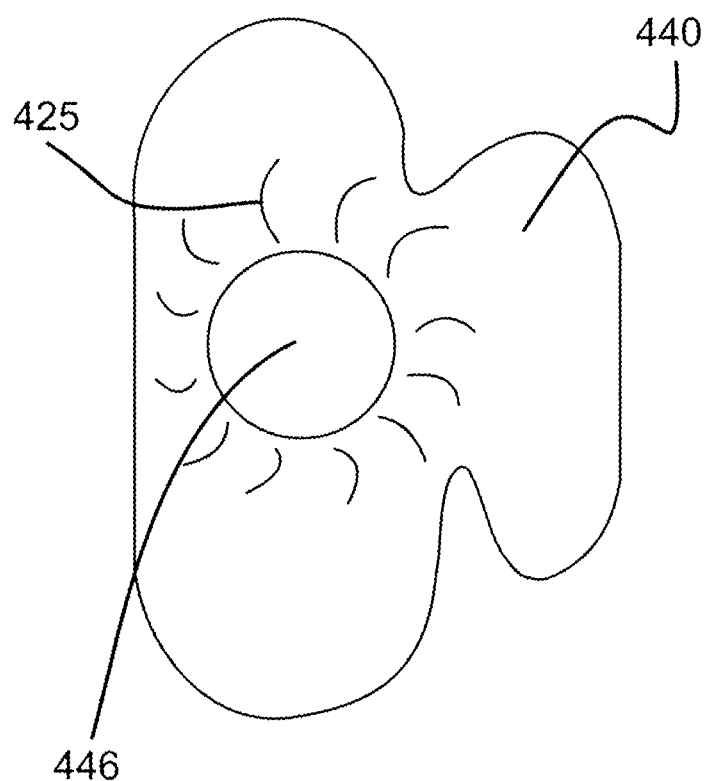
FIG. 26 is a front side view of the locking component of the spinous process fixation implant of FIG. 24.

In another embodiment of the spinous process fixation assembly 400, shown in FIG. 24, the front S-shaped plate include a top pivoting component 410, shown in FIG. 25A, and a bottom pivoting component 420, shown in FIG. 25B, forming the top and bottom portions of the S-curve, respectively. The back S-plate 430 is formed as one component S-shaped plate with a curved top portion 432, a bottom curved portion 434 and a rounded center 438 having an aperture formed in its center 436, shown in FIG. 25C. The top pivoting component 410 includes an upward extending curved portion 412 and a lower rounded end 414 having an aperture 416 formed in its center. The bottom pivoting component includes a downward extending curved portion 422 and an upper rounded end 424 having an aperture 426 formed in its center. The front and back surfaces of the rounded end 424, the back surface of the rounded end 414 and the front surface of the rounded center 438 have radial extending grooves 425, shown in FIG. 25B and FIG. 25C. Grooves 425 define one-degree arcs, thus allowing the plates 410, 420, 430 to rotate relative to each other by one degree steps. Assembly 400 further includes a block 440 dimensioned to fit between the adjacent spinous processes 90a, 90b and having top and bottom edges configured to correspond to the geometry of the spinous processes 90a, 90b and lamina around which they will fit once implanted. Different sized blocks are used to accommodate different spacings between adjacent spinous processes 90a, 90b. The front and back surfaces of block 440 also include grooves 425 around an aperture 446 formed n the center of the block. The top pivoting plate 410, bottom pivoting plate 420, block 440 and the back plate 430 are arranged so that their corresponding apertures 416, 426, 446, 436 are aligned and a bolt 480 is threaded through these apertures. Once the assembly 400 is inserted, the plates 410 and 420 are pivoted upward and downward, respectively, and are placed so as to surround the spinous processes. The inner surfaces of the upper and lower arms of the S-shaped plates are sculpted to fit the shape of the spinous processes and have protrusions that frictionally engage the sides of the spinous processes and together with the bolt 480 securely lock the assembly 400 between the spinous processes 90a, 90b.

Figure 27:
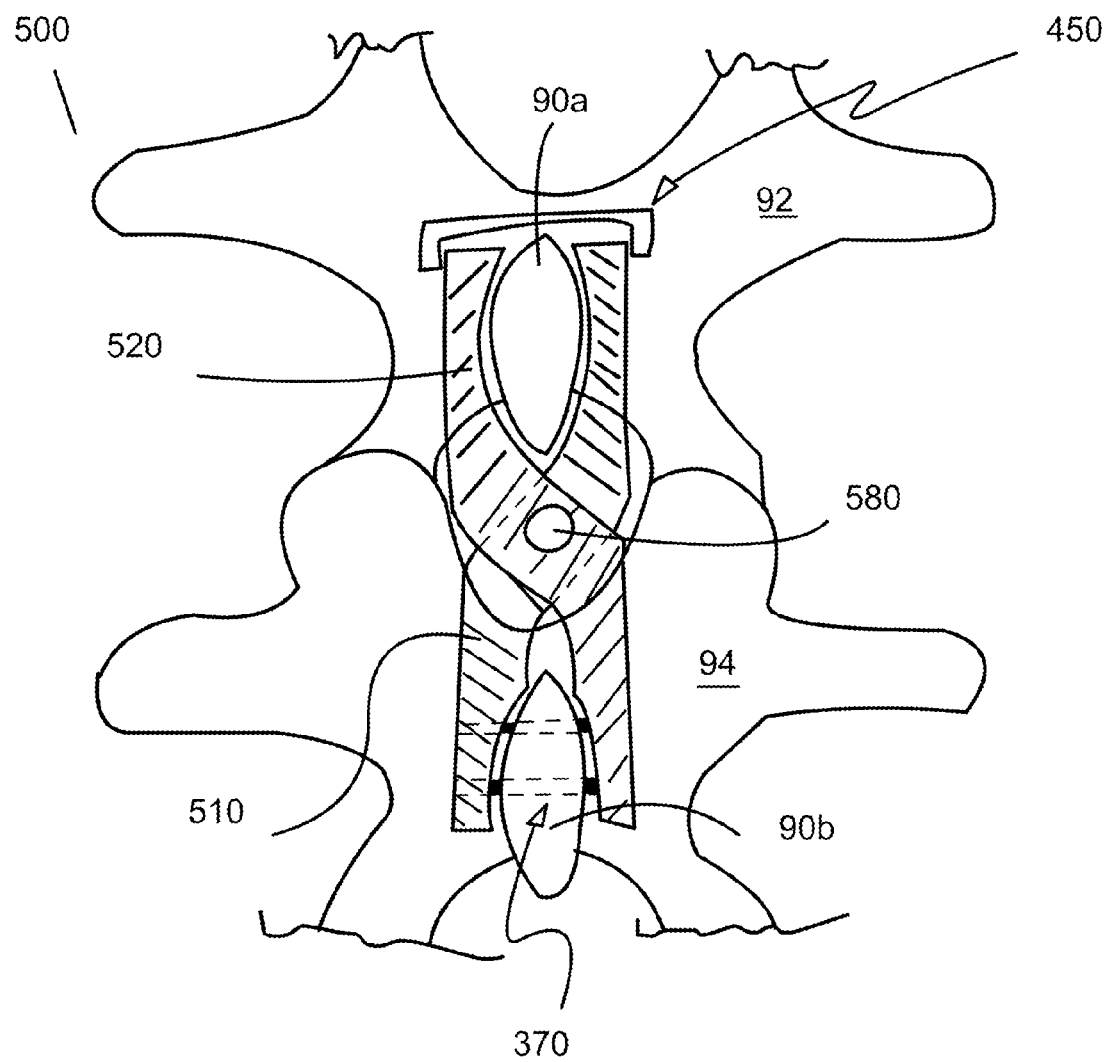
FIG. 27 is a front side view of a fifth embodiment of a spinous process fixation implant according to the present invention, depicting front and back pivoting components in the closed and locked position around the spinous processes.

Long bolts 370 may be also added to this embodiment to further anchor the assembly 400 on the spinous processes, as was described above. Alternatively, a staple 450 may be placed on the top and bottom open ends of the plates 410, 420 and 430, as shown in FIG. 27. In other embodiments banding, cabling or suturing may be used to attach the ends of plates 410, 420 and 430 to the spinous processes. The outer surfaces of the plates 410, 420 and 430 may be rounded, as shown in FIG. 24 or straight, a shown in the embodiment 500 of FIG. 27.

Figure 28:
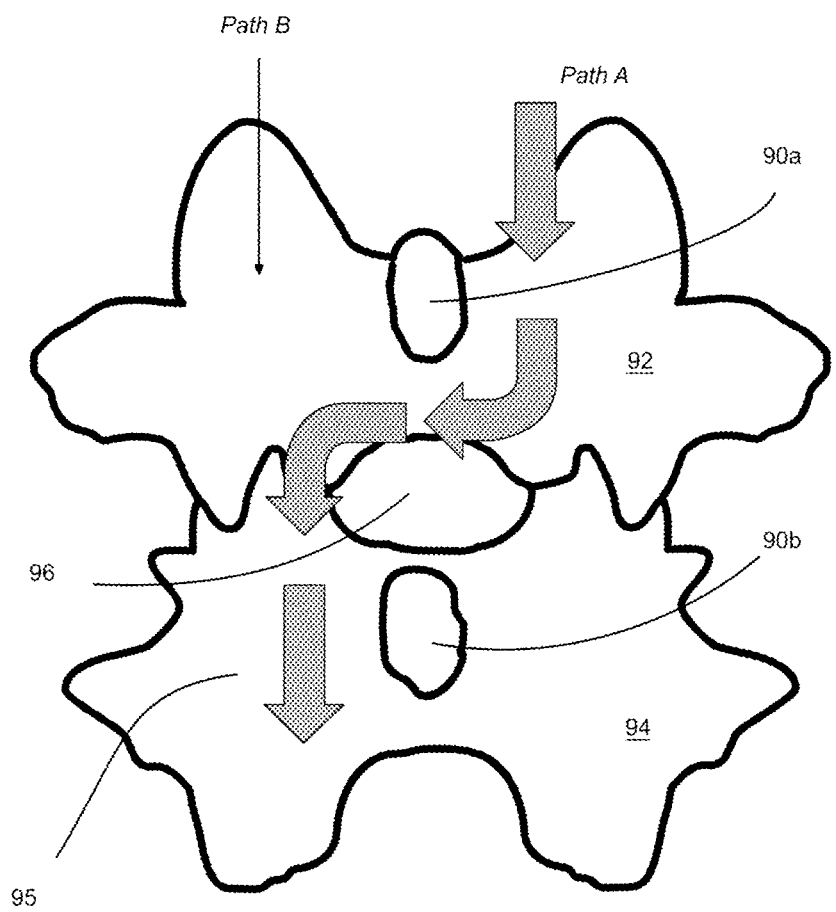
FIG. 28 depicts cutting and opening paths A and B around superior and inferior adjacent spinous processes.
Figure 29:
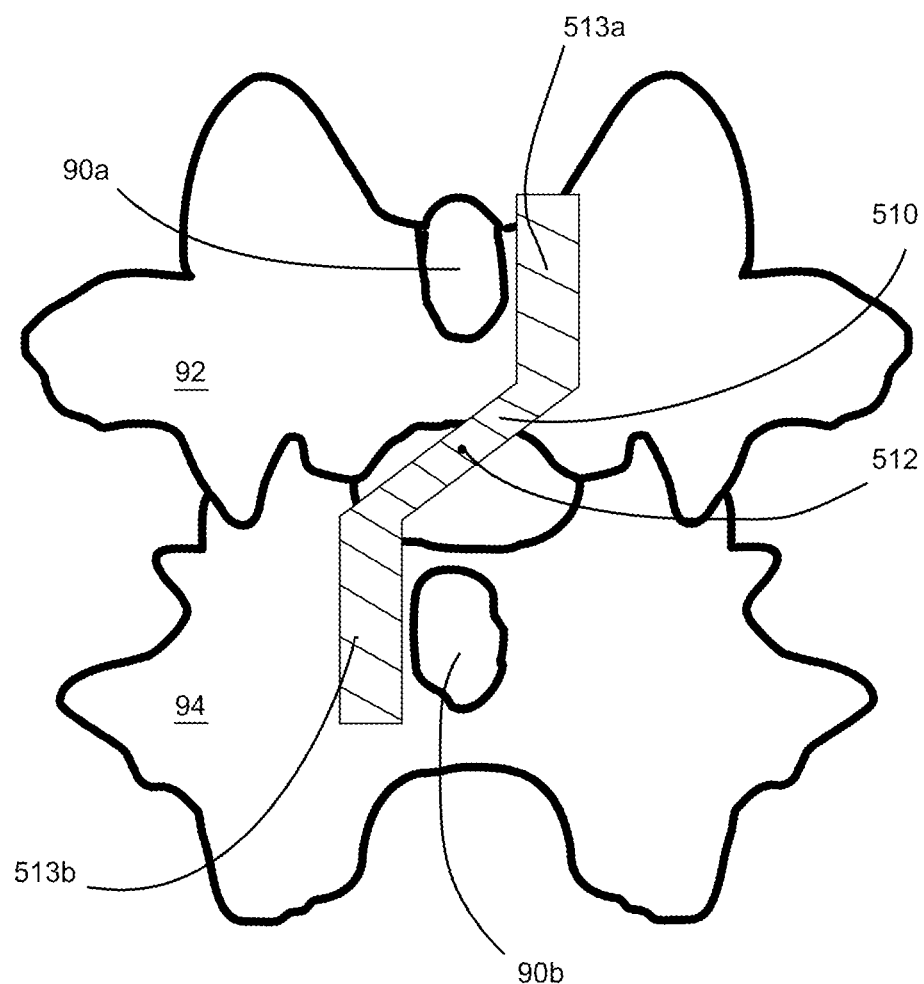
FIG. 29 depicts inserting back pivoting component of the spinous process fixation implant of FIG. 27 along path A of FIG. 28.
Figure 30:
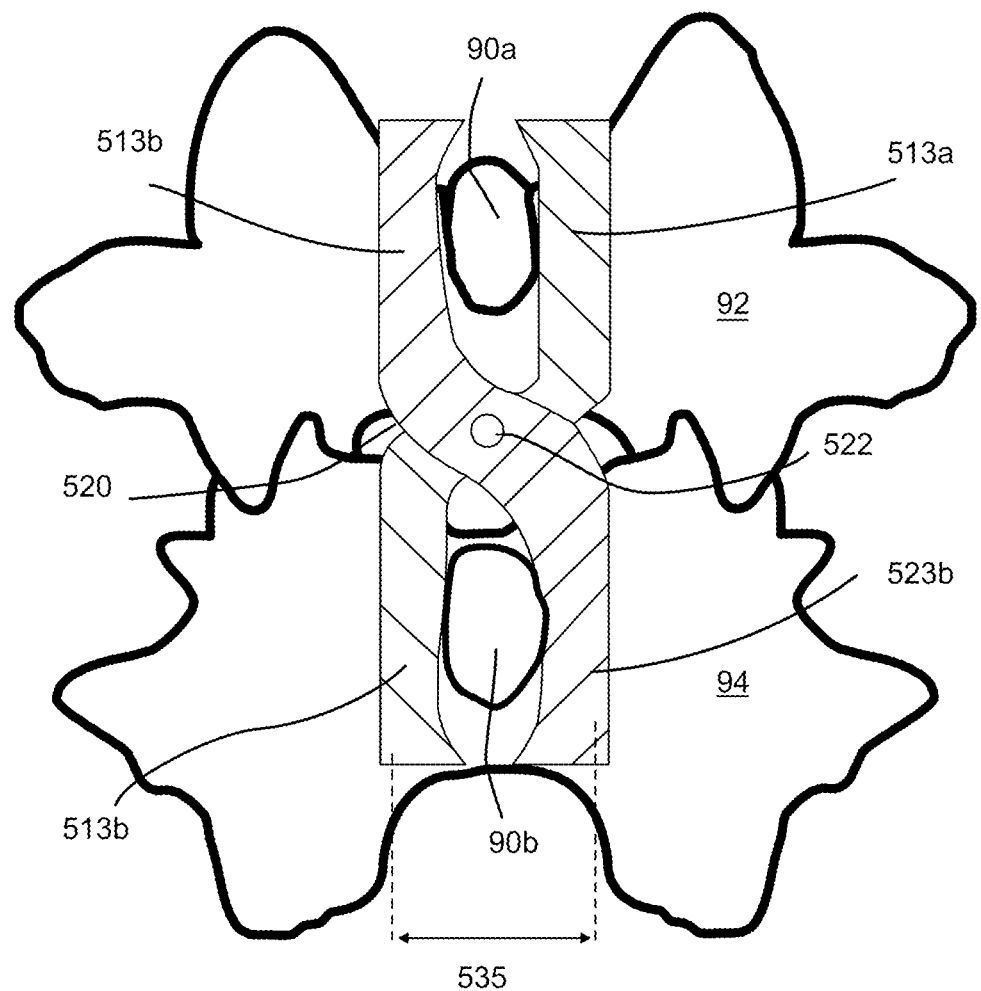
FIG. 30 depicts inserting front pivoting component of the spinous process fixation implant of FIG. 27 along path B of FIG. 28.

Referring to FIG. 28, FIG. 29 and FIG. 30, the process of implanting the spinous process fixation assembly between two adjacent vertebrae includes the following steps. First an incision is made in the patient's back and paths A and B are opened along bony planes 95 and through ligaments 96 between the adjacent spinous processes 90a, 90b. Path B is mirror image of path A about the centered sagittal plane 98. Next, the back component 510 of the assembly of FIG. 27 is inserted along path A, as shown in FIG. 29, and the ends 513a and 513b are attached to the spinous processes 90a, 90b, respectively. Next, the front component 520 is inserted along path B and a bolt 580 is threaded through the apertures 512, 522 formed in the centers of back and front components 510, 520, respectively. The front and back components are pivoted around the axis passing through their central apertures 512, 522, so that their ends 513a, 523a, 513b, 523b surround and close around the spinous processes 90a, 90b. The ends 513a, 523a, and 513b, 523b are then attached to spinous processes 90a, 90b, respectively as shown in FIG. 30. The ends may be attached with any of the above mentioned methods including frictional engagement of protrusions, long bolts, staples, cabling, banding or suturing. Plates 510, 520 are dimensioned so when assembled, assembly 500 has a width 535 that covers and protects the spinal cord after laminectomy or facectomy.

Figure 31:
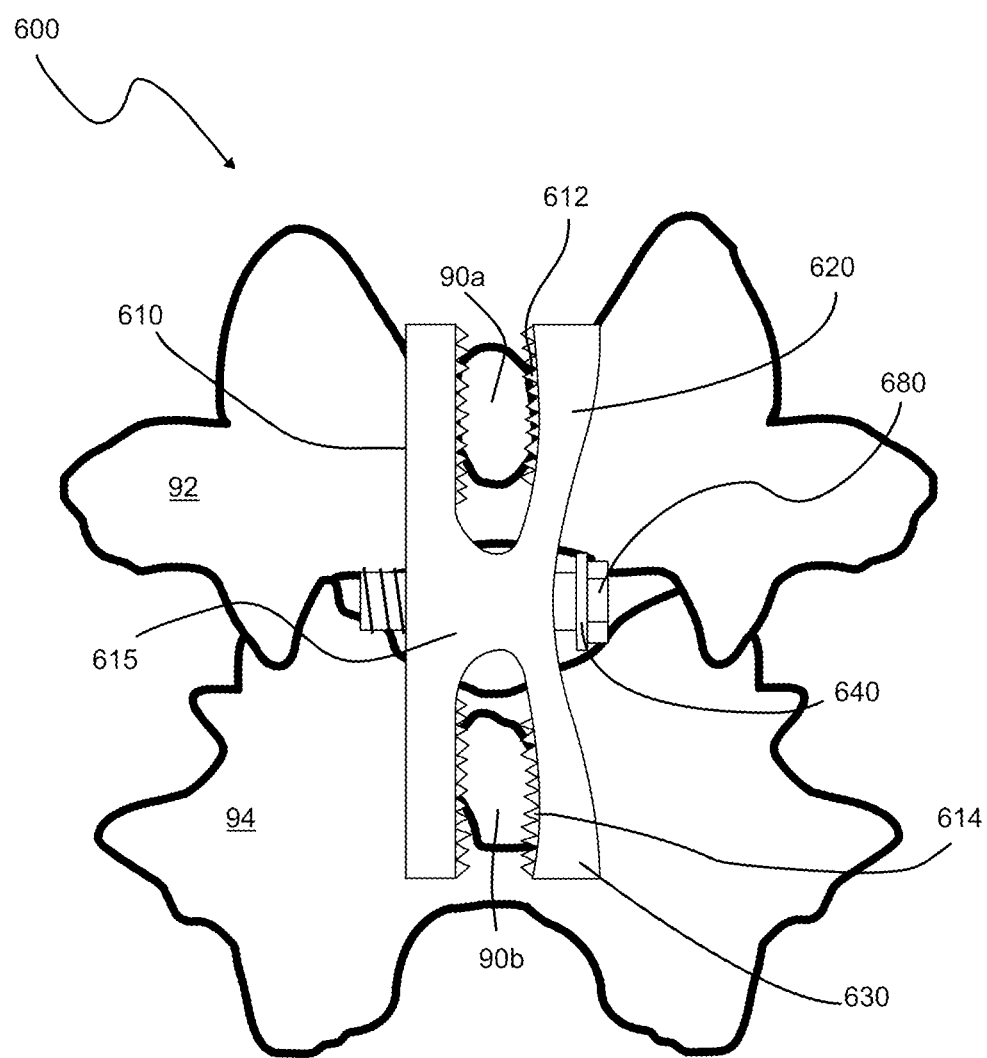
FIG. 31 is a front side view of a sixth embodiment of a spinous process fixation implant according to the present invention, depicting a single K-component body.

In a sixth embodiment, shown in FIG. 31, spinous process fixation assembly 600 includes one K-shaped component having an elongated plate 610 and two deformable plates 620, 630 extending upward and downward, respectively, from the center 615 of the elongated plate. A top gap 612 is formed between the top portion of the elongated plate 610 and the upward extending plate 620. A bottom gap 614 is formed between the bottom portion of the elongate plate 610 and the downward extending plate 630. The K-shaped assembly is placed between the adjacent spinous processes 90a, 90b, as shown in FIG. 31, and a plate 640 is placed in the center of the assembly 600 on top deformable plates 620, 630. A bolt 680 is threaded through apertures formed in the center of plate 640 and the center 615 of the K-shaped component, as shown in FIG. 31. Tightening of the bolt 680 down applies pressure onto the plate 640, which is transferred to the top and bottom deformable plates 620, 630. Plates 620, 630 move closer to plate 610 and the widths of the top and bottom gaps 612, 614 is reduced, resulting in engaging protrusions 111 formed on the inner surfaces of plates 610, 620, 630 with the spinous processes 90a, 90b and tightening of the plates 620, 630 and 610 around the spinous processes 90a, 90b. The ends of the plates 620, 630 may be further attached to the spinous processes with any of the above mentioned methods including long bolts, staples, cabling, banding or suturing.

Other embodiments are within the scope of the following claims. For example, vertebras 92 and 94 may be any two vertebras, including lumbar L1-L5, thoracic T1-T12, cervical C1-C7 or the sacrum. The fixation assembly 100 may extend along multiple vertebras. The K shaped structure may be also configured as a mirror image of the structure in FIG. 2, with the pivoting plates 120, 130 located on the left side and the elongated plate 110 located on the right side of the FIG. 2. The elongated plates 110, 220 and the top and bottom pivoting plates 120, 220, and 130, 230 of the embodiments of FIG. 4 and FIG. 15, respectively, may have adjustable lengths. Similarly, S-plates 310, 320 of the embodiment of FIG. 21 and plates 410, 420, 430 of the embodiment of FIG. 24 may have adjustable lengths. Similarly, elongated plate 610 and deformable plates 620, 630 of the embodiment of FIG. 31 may have adjustable lengths. The main bodies 122, 132 of pivoting plates 120, 130 may be detached from the corresponding extending arms 124, 134. Bodies 122, 132 may be attached to the extending arms 124, 134 via hinges (not shown) which allow them to swing open and close for better placement around the corresponding spinous processes 90a, 90b.

Several embodiments of the present invention have been described. Nevertheless, it will be understood that various modifications may be made without departing from the spirit and scope of the invention. Accordingly, other embodiments are within the scope of the following claims.

What is claimed is:

1. An implantable assembly for stabilization of spinous processes, comprising:
   a k-shaped component comprising an elongated plate and top and bottom deformable plates extending at non-zero value first and second angles from a first surface of said elongated plate, respectively, thereby defining first and second spaces between said elongated plate and said top and bottom deformable plates;
   a compression element configured to compress and move said first and second deformable plates toward said elongated plate and to change said first and said second angles, respectively; a top locking member placed over said elongated plate's top end and said top deformable plate's top end and configured to lock said elongated plate's top end and said top deformable plate's top end without passing through said first spinous process;
   wherein said first and second spaces are configured to receive first and second spinous processes, respectively; and
   wherein said moving of said first and second deformable plates toward said elongated plate results in engaging said first surface of said elongated plate and first surfaces of said top and bottom deformable plates with lateral surfaces of said first and second spinous processes, respectively.

2. The assembly of claim 1 wherein said compression element comprises a plate placed on top of said top and bottom deformable plates and a bolt configured to pass through concentrically aligned through-bore openings formed in the center of said plate, said top and bottom deformable plates and the center of said elongated plate.

3. The assembly of claim 2 wherein said bolt comprises a head having a diameter larger that the diameter of said plate's through-bore and an elongated body having threads formed at a portion of said elongated body, said threads being dimensioned to engage inner threads in said elongated plate's through-bore.

4. The assembly of claim 3 wherein tightening said bolt engages said bolt threads with said inner threads in said elongated plate's through-bore and compresses said head onto said plate and said plate onto said deformable top and bottom plates, causing them to move toward said elongated plate.

5. The assembly of claim 1 wherein said first surface of said elongated plate faces said first surfaces of said top and bottom deformable plates and said all first surfaces comprise protrusions configured to engage and frictionally lock said elongated plate's first surface and said deformable top and bottom plates' first surfaces onto said lateral surfaces of said first and second spinous processes.

6. The assembly of claim 5 wherein said protrusions are selected from a group consisting of teeth, spikes, serrations, rough coatings and ridges.

7. The assembly of claim 1 wherein said top locking member is selected from a group consisting of staples, cables, sutures, pins and screws.

8. The assembly of claim 1 further comprising a bottom locking member configured to lock said elongated plate's bottom end and said bottom deformable plate's bottom end.

9. The assembly of claim 8 wherein said bottom locking member comprises a long bolt configured to be threaded through bolt holes formed through said bottom deformable plate's bottom end, said second spinous process and said elongated plate's bottom end.

10. The assembly of claim 8 wherein said bottom locking member is selected from a group consisting of staples, cables, sutures, pins and screws.

11. The assembly of claim 1 wherein said elongated plate, said top and bottom deformable plates and said compression element comprise material selected from a group consisting of stainless steel, titanium, gold, silver, alloys thereof, absorbable material, non-metal materials including synthetic ligament material, polyethylene, extensible materials and combinations thereof.

12. The assembly of claim 1 wherein said elongated plate and said top and bottom deformable plates comprise adjustable lengths.

13. A method for stabilizing spinous processes, comprising:
providing a k-shaped component comprising an elongated plate and top and bottom deformable plates extending at non-zero first and second angles from a first surface of said elongated plate, respectively, thereby defining first and second spaces between said elongated plate and said top and bottom deformable plates, wherein said first and second spaces are configured to receive spinous processes, and a compression element configured to compresses and move said first and second deformable plates toward said elongated plate and to change said first and said second angles, respectively; a top locking member placed over said elongated plate's top end and said top deformable plate's top end and configured to lock said elongated plate's top end and said top deformable plate's top end without passing through said first spinous process;
placing first and second spinous processes within said first and second spaces, respectively; and
compressing and moving said first and second deformable plates toward said elongated plate via said compression element, thereby engaging lateral surfaces of said first and second spinous processes onto said elongated plate's first surface and said first and second deformable plates' first surfaces, respectively.

14. The method of claim 13 wherein said compression element comprises a plate placed on top of said top and bottom deformable plates and a bolt configured to pass through concentrically aligned through-bore openings formed in the center of said plate, said top and bottom deformable plates and the center of said elongated plate.

15. The method of claim 14 wherein said bolt comprises a head having a diameter larger that the diameter of said plate's through-bore and an elongated body having threads formed at a portion of said elongated body, said threads being dimensioned to engage inner threads in said elongated plate's through-bore.

16. The method of claim 15 further comprising tightening said bolt to engage said bolt threads with said inner threads in said elongated plate's through-bore and to compresses said head onto said plate and said plate onto said deformable top and bottom plates, thereby causing them to move toward said elongated plate.

17. The method of claim 16 wherein said first surface of said elongated plate faces said first surfaces of said top and bottom deformable plates and all said first surfaces comprise protrusions configured to engage and frictionally lock said first elongated plate surface and said first surfaces of said top and bottom deformable plates onto said lateral surfaces of said first and second spinous processes.

18. The method of claim 17 wherein said protrusions are selected from a group consisting of teeth, spikes, serrations, rough coatings and ridges.

19. The method of claim 13 wherein said top locking member is selected from a group consisting of staples, cables, sutures, pins and screws.

20. The method of claim 13 further comprising providing a bottom locking member configured to lock said elongated plate's bottom end and said bottom deformable plate's bottom end.

21. The method of claim 20 wherein said bottom locking member comprises a long bolt configured to be threaded through bolt holes formed through said bottom deformable plate's bottom end, said second spinous process and said elongated plate's bottom end.

22. The method of claim 20 wherein said bottom locking member is selected from a group consisting of staples, cables, sutures, pins and screws.

23. The method of claim 13 wherein said elongated plate, said top and bottom deformable plates and said compression element comprise material selected from a group consisting of stainless steel, titanium, gold, silver, alloys thereof, absorbable material, non-metal materials including synthetic ligament material, polyethylene, extensible materials and combinations thereof.

24. The method of claim 13 wherein said elongated plate, said top and bottom deformable plates comprise adjustable lengths.

* * * * *